(12) United States Patent
Mickiewicz et al.

(10) Patent No.: US 8,969,017 B2
(45) Date of Patent: Mar. 3, 2015

(54) METABOLITE BIOMARKERS FOR DIAGNOSIS AND PROGNOSIS OF PEDIATRIC SEPTIC SHOCK

(71) Applicants: UTI Limited Partnership, Calgary (CA); Children's Hospital Medical Center, Cincinnati, OH (US)

(72) Inventors: Beata Mickiewicz, Calgary (CA); Hans J. Vogel, Calgary (CA); Hector R. Wong, Calgary (CA); Brent W. Winston, Calgary (CA)

(73) Assignees: UTI Limited Partnership, Calgary, Alberta (CA); Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 14/160,712

(22) Filed: Jan. 22, 2014

(65) Prior Publication Data
US 2014/0205591 A1 Jul. 24, 2014

Related U.S. Application Data

(60) Provisional application No. 61/755,347, filed on Jan. 22, 2013.

(51) Int. Cl.
*G01N 33/53* (2006.01)
*G01N 31/00* (2006.01)
*G01R 33/465* (2006.01)

(52) U.S. Cl.
CPC .................................. *G01R 33/465* (2013.01)
USPC ........... 435/7.21; 435/7.1; 436/501; 436/518; 424/9.1; 424/520; 530/300; 530/350

(58) Field of Classification Search
None
See application file for complete search history.

(56) References Cited

PUBLICATIONS

Aneja and Carcillo, "Differences between adult and pediatric septic shock," *Minerva Anestesiol*, 77:986-92, 2011.
Bruins et al., "In vivo measurement of nitric oxide production in porcine gut, liver and muscle during hyperdynamic endotoxaemia," *Br. J. Pharmacol.*, 137(8): 1225-36, 2002.
Eriksson et al., In: *Multi- and Megavariate Data Analysis Part I: Basic Principles and Applications*, Umeå, Sweden: Umetrics AB, 2006.
Goldman "The clinical evaluation of renal function," *Calif. Med.*, 85(6): 376-80, 1956.
Goldstein et al., "International pediatric sepsis consensus conference: definitions for sepsis and organ dysfunction in pediatrics," *Pediatr. Crit. Care Med.*, 6(1): 2-8, 2005.
Hasselgren et al., "Protein metabolism in different types of skeletal muscle during early and late sepsis in rats," *Arch. Surg.*, 121(8): 918-23, 1996.
Izquierdo-Garcia et al., "A metabolomic approach for diagnosis of experimental sepsis," *Intensive Care Med*, 2011.
Knowles and Moncada, "Nitric oxide synthases in mammals," *Biochem. J.*, 298 (Pt 2): 249-58, 1994.
Kovarik et al., "Effects of beta-hydroxy-beta-methylbutyrate treatment in different types of skeletal muscle of intact and septic rats," *J. Physiol. Biochem.*, 66(4): 311-9, 2010.
Kramer R, In: *Chemometric techniques for quantitative analysis*, New York, USA: Marcel Dekker, Inc., 1998.
Lin et al., "A metabonomic approach to early prognostic evaluation of experimental sepsis by (1)H NMR and pattern recognition," *NMR Biomed.*, 22(6): 601-8, 2009.
Trygg and Wold, "Orthogonal projections to latent structures (O-PLS)," *J. Chemometrics*, 16(3): 119-28, 2002.
Wannemacher et al., "The significance and mechanism of an increased serum phenylalanine-tyrosine ratio during infection," *Am. J. Clin. Nutr.*, 29(9): 997-1006, 1976.
Weljie et al., "Targeted profiling: quantitative analysis of 1H NMR metabolomics data," *Anal Chem.*, 78(13): 4430-42, 2006.
Wishart et al., "HMDB: a knowledgebase for the human metabolome," *Nucleic Acids Res.*; 37(Database issue): D603-10, 2009.
Wu et al., "Dietary protein or arginine deficiency impairs constitutive and inducible nitric oxide synthesis by young rats," *J. Nutr.*, 129(7): 1347-54, 1999.
Wynn et al., "The influence of developmental age on the early transcriptomic response of children with septic shock," *Mol. Med.*, 17(11-12): 1146-56, 2011.
Xu et al., "A metabonomic approach to early prognostic evaluation of experimental sepsis," *J Infect.*, 56(6): 474-81, 2008.

*Primary Examiner* — Lisa Cook
(74) *Attorney, Agent, or Firm* — Parker Highlander PLLC

(57) ABSTRACT

The present invention provides methods for differentiating a pediatric subject with pediatric septic shock from a healthy pediatric subject or one having sudden inflammatory response syndrome (SIRS). Also provided is a method of predicting pediatric septic shock mortality in a pediatric septic shock patient.

20 Claims, 15 Drawing Sheets
(12 of 15 Drawing Sheet(s) Filed in Color)

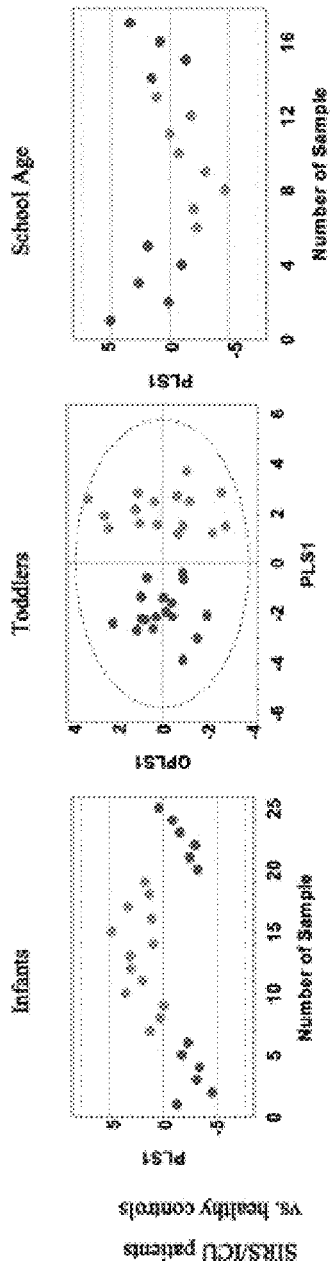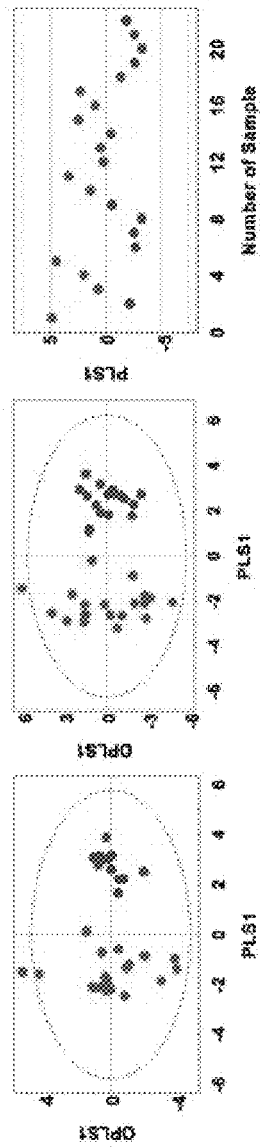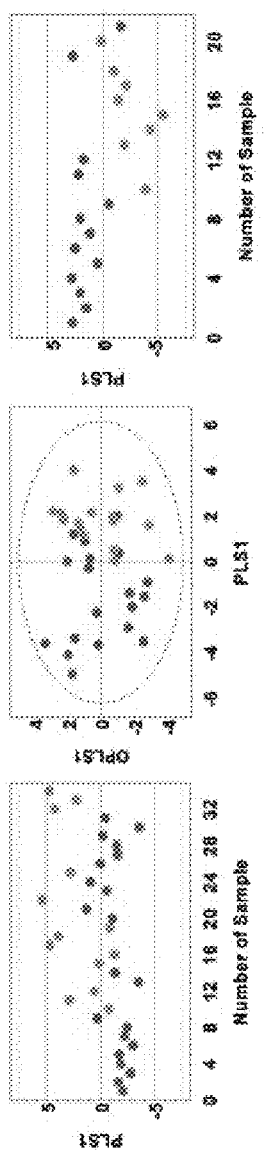
FIGS. 3A-C

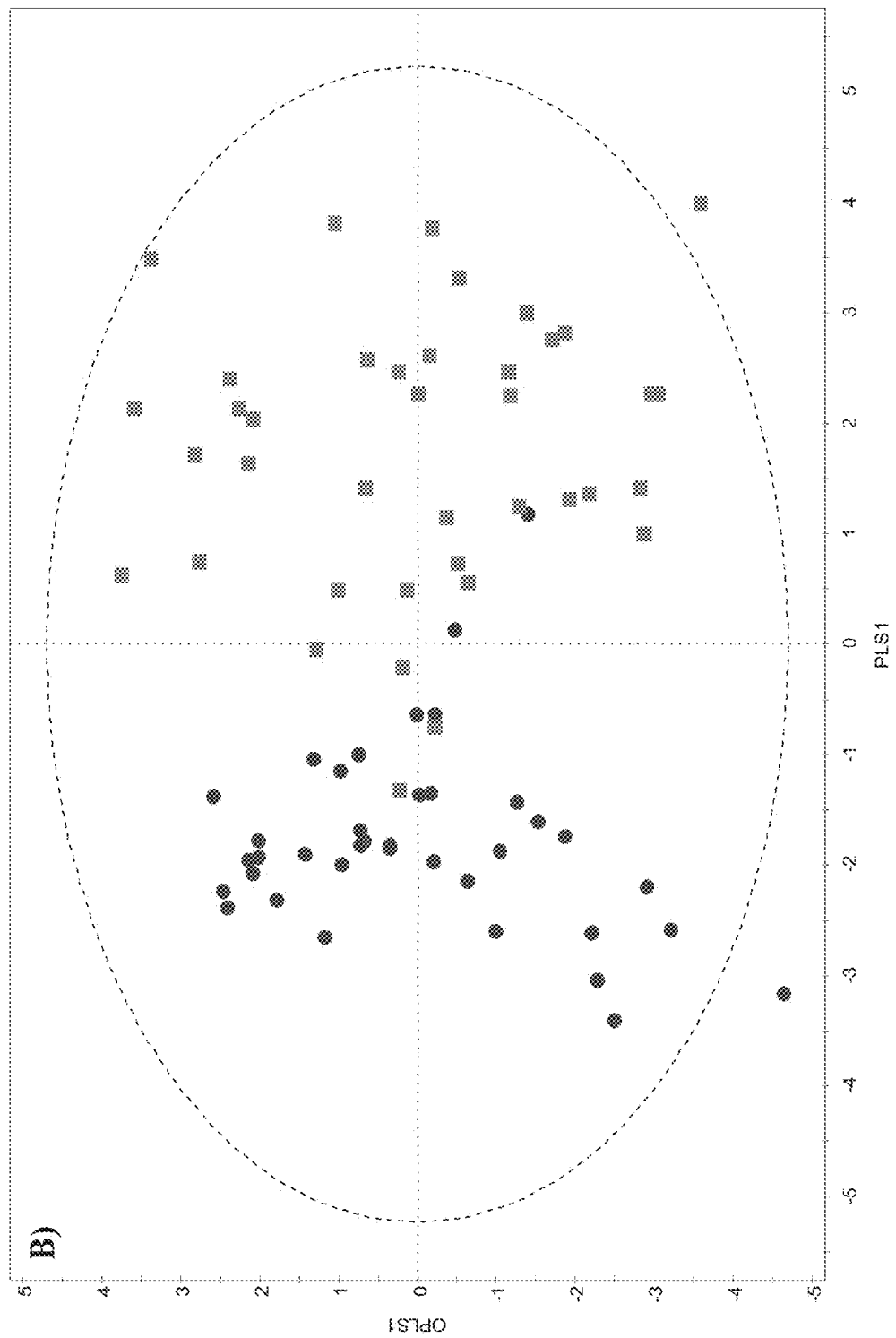

METABOLITE BIOMARKERS FOR DIAGNOSIS AND PROGNOSIS OF PEDIATRIC SEPTIC SHOCK

This application claims benefit of priority to U.S. Provisional Application Ser. No. 61/755,347, filed Jan. 22, 2013, the entire contents of which are hereby incorporated by reference.

BACKGROUND

1. Field of the Invention

This document relates to methods and materials for assessing metabolite biomarker useful in the diagnosis and prognosis of pediatric septic shock. In particular, the methods comprise the use of $^1$H-NMR to assess serum metabolites characteristic of septic shock vs normal controls or ICU (SIRS) non-septic controls and to assess serum metabolites that characterize prognosis (i.e. to determine those who will die from those who will not).

2. Background of the Invention

In the 1980's, the death rate from septic shock in children was around 50% [1, 2], but over the past few decades, with the best of early diagnosis and therapy, it has decreased to ~10% [3, 4]. Unfortunately, in third world countries the mortality rate remains extremely high [5,6]. Moreover, every hour of septic shock without appropriate resuscitation and restoration of blood pressure increases mortality risk by 40% [7]. Septic shock is a very dynamic process and the clinical status of a child may deteriorate quickly [8]. The first hours following the diagnosis are called the "golden hours" for patients' survival, therefore aggressive and goal-directed treatment should be initiated as quickly as possible [9]. It is reported that those children in whom septic shock is recognized early and properly treated have a much higher survival rate than children who were diagnosed later [10-12]. Thus, developing diagnostic approaches that might accelerate disease recognition is extremely important in order to improve patients' outcomes and decrease mortality.

SUMMARY OF THE INVENTION

Here, the inventors provide the first evidence that a serum metabolomics fingerprint will identify pediatric patients that have septic shock and a provide fingerprint that will identify early (within 24 hours) those who will likely die from their disease.

Thus, in accordance with the present invention, there is provided a method of differentiating a pediatric subject with pediatric septic shock from a healthy pediatric subject comprising (a) obtaining a serum sample from said subject; (b) subjecting said sample to nuclear magnetic resonance (NMR) analysis of 2-hydroxybutyrate, 2-hydroxyisovalerate and lactate levels, and (c) diagnosing said subject has having pediatric septic shock when 2-hydroxybutyrate, 2-hydroxyisovalerate and lactate levels in said subject are elevated as compared to levels in a healthy pediatric subject.

The subject may be an infant or toddler. The method may further comprise NMR analysis of 2-aminobutyrate, 2-oxoisocaproate, glucose, creatinine and/or phenylalanine. The method may further comprise NMR analysis of 2-methylglutarate, acetone, adipate, arginine, betaine, carnitine, citrate, creatine, creatine phosphate, glutamine, histidine, hypoxanthine, isobutyrate, myo-inositol, o-acetylcarnitine and/or threonine. The method may further comprise treating said subject for pediatric septic shock when diagnosed as having pediatric septic shock.

In another embodiment, there is provided a method of differentiating a pediatric subject with sudden inflammatory response syndrome (SIRS) from a healthy subject having comprising (a) obtaining a serum sample from said subject; (b) subjecting said sample to nuclear magnetic resonance (NMR) analysis of methanol and citrate, and (c) diagnosing said subject has having SIRS when levels of methanol and citrate are reduced as compared to levels in a healthy pediatric subject.

The subject may be an infant, toddler or school age. The method may further comprise NMR analysis of 2-aminobutyrate, acetone, glutamine, lactate, and/or phenylalanine. The method may further comprise NMR analysis of 2-hydroxyisobutyrate, 2-hydroxyisovalerate, 2-oxoisocaproate, 2-hydroxybutyrate, 3-hydroxyisovalerate, acetate, alanine, arginine, creatine phosphate, creatinine, ethanol, glycerol, glycerin, isobutyrate, myo-inositol, pyroglutamate, pyruvate, suberate, taurine, tyrosine and/or urea. The method may further comprise treating said subject for SIRS when diagnosed as having SIRS.

In yet another embodiment, there is provided a method of predicting mortality in a pediatric sepsis patient comprising (a) obtaining a serum sample from said subject; (b) subjecting said sample to nuclear magnetic resonance (NMR) analysis of lactate, alanine, creatine phosphate, 2-methylglutarate, urea, serine and aspartate levels, and (c) predicting mortality in said subject when lactate, alanine, creatine phosphate and 2-methyglutarate levels in said subject are elevated, and urea, serine and aspartate levels are reduced, both as compared to levels observed in pediatric septic shock survivors.

The subject may be an infant, toddler or school age. The method may further comprise NMR analysis of propylene glycol, 2-oxoglutarate, 2-hydroxyisovalerate and/or methanol. The method may further comprise NMR analysis of 2-aminobutyrate, citrate, proline, glycerol, glycine, isopropanol, threonine, dimethyl sulfone, ornithine, glutamine and/or creatine. The method may further comprise treating said subject for pediatric septic shock.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one." "About" means plus or minus 5% of the stated value.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The patent or application file contains at least one drawing executed in color. Copies of this patent or patent application publication with color drawings will be provided by the Office upon request and payment of the necessary fee.

FIGS. 3A-C. The OPLS-DA score scatter plots for models consisting of two classes. (FIG. 3A) SIRS/ICU controls vs. healthy controls; (FIG. 3B) septic shock patients vs. healthy controls; (FIG. 3C) septic shock patients vs. SIRS/ICU controls within three different age groups: infants, toddlers and school age children. Septic shock patients are marked in red, SIRS/ICU controls in green and healthy controls in blue.

FIGS. 5A-C. The OPLS-DA score scatter plots for models consisting of two classes. (FIG. 5A) septic shock patients and healthy controls; (FIG. 5B) SIRS/ICU patients and healthy controls; (FIG. 5C) septic shock patients and SIRS/ICU controls. Septic shock patients are marked by triangles, SIRS/ICU controls by squares and healthy controls by dots.

(FIG. 6A) OPLS-DA score scatter plot, and (FIG. 6B) "Observed vs. Predicted" plot, for survivors (light triangles) and non-survivors (dark triangles) from 20 septic shock patients (10 non-survivors and 10 age- and gender-matched survivors) based on the metabolomics data set. Both groups are separated along the first PLS component and none of non-survival patients was predicted as a survivor. The potentially important metabolites were chosen in 2-sample t-tests with a threshold of p<0.2.

(FIG. 7A) OPLS-DA score scatter plot and (FIG. 7B) "Observed vs. Predicted" plot for survivors (light triangles) and non-survivors (dark triangles) from septic shock patient group associated with complicated course (23 serum samples) based on the metabolomics data set. Both groups are very well separated and none of non-survivors was predicted as a survivor. The potentially important metabolites were chosen in 2-sample t-tests with a threshold value of p<0.2.

(FIG. 8A) The column plot shows the changes in serum metabolite concentrations in septic shock specimens (10 septic shock non-survivors and 10 age- and gender-matched septic shock survivors). Positive values of coefficients (the upper part of the diagram) indicate increased metabolite concentrations in non-survivors while negative values (the lower part of diagram) present a decrease in metabolite concentrations in non-survivors, as compared to age- and gender-matched septic shock survivors. (FIG. 8B) The column plot shows the changes in serum metabolite concentrations in septic shock patients with a complicated course. Positive values of coefficients (the upper part of the diagram) indicate increased metabolite concentrations in non-survivors while negative values (the lower part of diagram) present a decrease in metabolite concentrations in non-survivors, as compared survivors.

DETAILED DESCRIPTION

In this study, the inventors assessed whether a metabolomics approach was possible for the diagnosis and prognosis of pediatric septic shock. Metabolomics is generally defined as "the quantitative measurement of the metabolic response of living systems to pathophysiological stimuli or genetic modification" [13, 14] and is based on analytical platforms such as proton nuclear magnetic resonance spectroscopy ($^1$H NMR) and/or mass spectrometry (MS) [13, 14]. It has been described that metabolomics is a very efficient tool for discovering biomarkers of various infectious diseases; for example severe childhood pneumonia [15] or hepatitis C virus infection [16].

Figure 4:
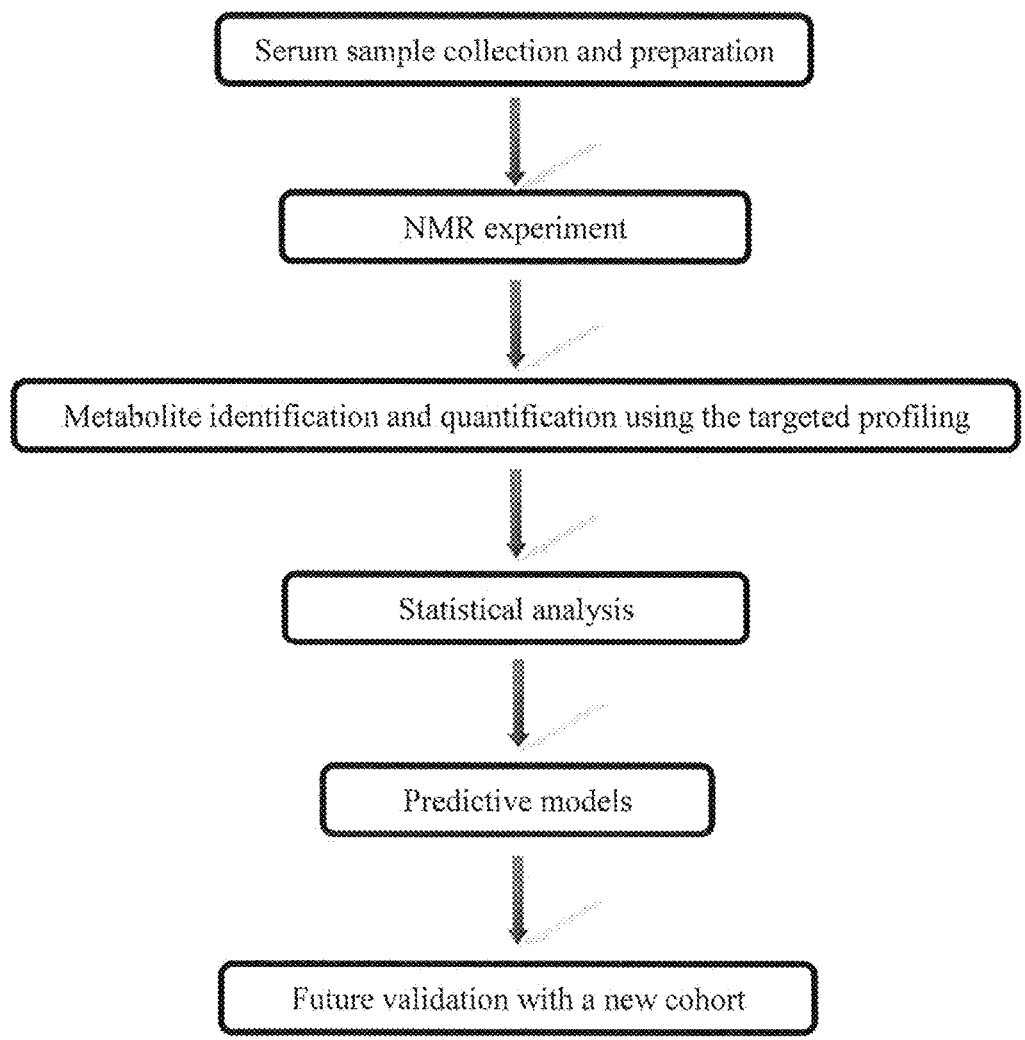
FIG. 4. The methodology of metabolomics analysis used in the study.

So far, most of metabolomics studies associated with sepsis have been reported for animal models [17-19] and there have been no published metabolomics studies of pediatric septic shock. In the present study, the inventor used $^1$H NMR and computational analysis to detect and measure concentrations of different metabolites in pediatric serum samples (FIG. 4). A single $^1$H NMR spectrum might be described as a complex distribution of unique spectral intensities from individual metabolites, which are identified and quantified during a process called targeted profiling [20]. Determined metabolite concentrations provided a dataset on which multivariate statistical analysis was performed. Techniques such as Principal Component Analysis (PCA) [21, 22], Partial Least Squares Discriminant Analysis (PLS-DA) [23] and Orthogonal Partial Least Squares Discriminant Analysis (OPLS-DA) [22] were applied in order to separate metabolic variation in the studied specimens. The results highlighted and separated metabolic changes in septic shock and those associated with increased mortality from metabolites identified in healthy and ICU (SIRS) control pediatric serum samples. This present study provides a promising application for early diagnosis and prognosis of septic shock in the PICU.

I. Pediatric Systemic Inflammation

A. Pediatric Septic Shock

Septic shock is a medical condition as a result of severe infection and sepsis, though the microbe may be systemic or localized to a particular site. It can cause multiple organ dysfunction syndrome (formerly known as multiple organ failure) and death. Its most common victims are children (pediatric septic shock), immunocompromised individuals, and the elderly, as their immune systems cannot deal with the infection as effectively as those of healthy adults. Generally, patients suffering from septic shock are cared for in intensive care units. The mortality rate from septic shock is approximately 25-50%.

In humans, septic shock has a specific definition requiring several conditions to be met for diagnosis. First, SIRS (systemic inflammatory response syndrome) must be diagnosed by finding at least two of the following:

tachypnea (high respiratory rate)>20 breaths per minute, or on blood gas, a $PCO_2$ less than 32 mmHg signifying hyperventilation;

white blood cell count either significantly low, <4000 cells/$mm^3$ or elevated >12000 cells/$mm^3$;

heart rate >90 beats per minute;

temperature: fever >38.5° C. (101.3° F.) or hypothermia <35.0° C. (95.0° F.)

Second, there must be sepsis (an infection) and not an alternative form/cause of SIRS. Sepsis requires evidence of infection, which may include positive blood culture, finding a microorganism in a normally sterile site, signs of pneumonia on chest x-ray, or other radiologic or laboratory evidence of infection. Third, severe sepsis is defined, in addition to the findings above, having evidence of end-organ dysfunction such as renal failure, liver dysfunction, changes in mental status, or elevated serum lactate. Finally, septic shock is diagnosed if, in addition to the features above, there is refractory hypotension (low blood pressure that does not respond to giving IV fluids). This signifies that intravenous fluid administration alone is insufficient to maintain a patient's blood pressure from becoming hypotensive and that drugs that raise the blood pressure are required.

Septic shock is a subclass of distributive shock, shock refers specifically to decreased tissue perfusion resulting in ischemia and organ dysfunction. Cytokines released in a large scale inflammatory response results in massive vasodilation, increased capillary permeability, decreased systemic vascular resistance, and hypotension. Hypotension reduces tissue perfusion pressure causing tissue hypoxia. Finally, in addition to decreased blood pressure, in septic shock, ventricular dilatation and myocardial dysfunction may occur.

When bacteria or viruses are present in the bloodstream, the condition is known as bacteremia or viremia. Sepsis is a constellation of symptoms secondary to infection that manifest as disruptions in heart rate, respiratory rate, temperature and WBC. If sepsis worsens to the point of end-organ dysfunction (renal failure, liver dysfunction, altered mental status, or heart damage), the condition is called severe sepsis. Once severe sepsis worsens to the point where blood pressure can no longer be maintained with intravenous fluids alone, then the criteria have been met for septic shock. The precipitating infections which may lead to septic shock if severe enough may include but are not limited to appendicitis, pneumonia, bacteremia, diverticulitis, pyelonephritis, meningitis, pancreatitis, and necrotizing fasciitis.

Approximately half the cases of septic shock are caused by endotoxin-producing Gram-negative bacteria. Endotoxins are bacterial wall lipopolysaccharides (LPS) consisting of a toxic fatty acid (lipid A) core common to all Gram-negative bacteria, and a complex polysaccharide coat (including O antigen) unique for each species. Analogous molecules in the walls of Gram-positive bacteria and fungi can also elicit septic shock. Free LPS attaches to a circulating LPS-binding protein, and the complex then binds to a specific receptor (CD14) on monocytes, macrophages, and neutrophils. Engagement of CD14 (even at doses as minute as 10 pg/mL) results in intracellular signaling via an associated "Toll-like receptor" protein 4 (TLR-4), resulting in profound activation of mononuclear cells and production of potent effector cytokines such as IL-1β and TNF-α. These cytokines act on endothelial cells and have a variety of effects including reduced synthesis of anticoagulation factors such as tissue factor pathway inhibitor and thrombomodulin. The effects of the cytokines may be amplified by TLR-4 engagement on endothelial cells. TLR-mediated activation helps to trigger the innate immune system to efficiently eradicate invading microbes. At high levels of LPS, the syndrome of septic shock supervenes; the same cytokine and secondary mediators, now at high levels, result in systemic vasodilation (hypotension), diminished myocardial contractility, widespread endothelial injury and activation, causing systemic leukocyte adhesion and diffuse alveolar capillary damage in the lung and also activation of the coagulation system, culminating in disseminated intravascular coagulation (DIC). The hypoperfusion resulting from the combined effects of widespread vasodilation, myocardial pump failure, and DIC causes multiorgan system failure that affects the liver, kidneys, and central nervous system, among others. Unless the underlying infection (and LPS overload) is rapidly brought under control, the patient usually dies.

Treatment primarily involves the following:
volume resuscitation
early antibiotic administration
early goal directed therapy
rapid source identification and control
support of major organ dysfunction Among the choices for vasopressors, norepinephrine is superior to dopamine in septic shock. Both however are still listed as first line in guidelines. Anti-mediator agents may be of some limited use in severe clinical situations however are controversial. Low dose steroids (hydrocortisone) for 5-7 days have been argued to lead to improved outcomes. Recombinant activated protein C (drotrecogin alpha) was found, in all but one report, not to decrease mortality and thus was not recommended for use. Other studies, however, comment that it may be effective in those with very severe disease. The first and only activated protein C drug, drotrecogin alfa (Xigris), was voluntarily withdrawn in October of 2011 after it failed to show a benefit in patients with septic shock, including the more severe disease subgroups.

1. Differences Between Adult and Pediatric Sepsis

There are considered to be four basis differences between the manifestation of sepsis in adults versus children: (a) developmental differences in the hemodynamic response; (b) activated Protein C; (c) thrombocytopenia-associated multiple organ failure; and (d) hemophagocytic lymphohistiocytosis (HLH).

With regard to hemodynamic response, almost 90% of adults present with "warm shock," characterized by low systemic vascular resistance, hypotension, normal or increased cardiac output, tachycardia and elevated oxygen in pulmonary artery blood. In contrast, children tend to exhibit "cold shock" characterized by severe hypovolemia, low CO, elevated SVR and cold clamped down extremities.

Protein C is a soluble, vitamin K-dependent, plasma serine protease that plays a central role in endogenous anti-coagulation. Its activated form is a potent enzyme and is capable of inactivating clotting co-factors Va and VIIIa and plasminogen-activator inhibitor 1. Reduced levels of Protein C and APC are associated with an increase chance of death in severe sepsis. Several studies indicated that use of APC therapy is beneficial in adults, but not in children, and in fact there may be increased adverse outcomes with pediatric administration of APC.

Thrombocytopenia-associated multiple organ failure is a thrombotic microangiopathic syndrome defined by a spectrum of pathology including thrombotic thrombocytic purpura (TTP), secondary thrombotic microangiopathy and disseminated intravascular coagulation. In general, this condition is treated with plasma exchange in children, but not in adults. In adults plasmapheresis is used. However, the treatment differences observed may be more a result of the difficulty in achieving plasma exchange in an adult given the volumes involved.

HLH is a non-malignant, inflammatory disorder resulting from persistent and excessive activation of antigen presenting cells and T lymphocytes. HLH is both familial and secondary, with the latter being associated with sepsis and infection. The prolonged activation of these cells can lead to elevated serum levels of pro-inflammatory cytokines such as TNF-α, IL-β, IL-6 and IL-8 which lead to inflammation, progressive cell death, organ dysfunction, and death. At present, HLH is still considered to be a pediatric disorder, but studies have reported the condition in adults as well.

HUH (Hemolytic Uremic Syndrome; also called 'hamburger disease') can be acquired eating food containing *E. coli* type 0157-H7. This disease is very much like TTP but is cause by infection. It tends to cause renal failure predominantly. This tends to be an adult disorder.

2. Treatment of Pediatric Sepsis

Treatment for pediatric sepsis is ideally rapid and based on time from initial diagnosis, as it is well established that delays in onset of therapy are directly related to mortality. The most immediate treatments (0-5 mins) involve 100% oxygen at high flow rate (15 L), intubation if necessary in neonates and infants, and breathing assistance as necessary, including mechanical ventilation. Next, it is critical to establish intravenous access followed by fluid and electrolyte resuscitation, as well as correcting any observed hyopglycemia to hypocalcemia The next phase of therapy, taking place in the first hour, should be antibiotics when infection is suspected (before cultures confirm infection) and directed towards the microorganisms most likely causing the infection, with dosing varying by age and weight. In addition, for fluid refractory shock, after fluid resuscitation, initiate vasopressor therapy titrated to correct hypotension; however, poor perfusion may well continue. Central line placement and arterial monitoring should be established. Warm shock (warm extremities, flash capillary refill) should receive norepinephrine 0.1-2 mcg/kg/min IV/IO infusion, titrated to desired effect, while cold shock (cool extremities, delayed capillary refill): receives epinephrine 0.1-1 mcg/kg/min IV/IO infusion, titrated to desired effect If shock persists following vasopressor initiation (60 min), one should continue with fluid replacement and obtain CVP measurement to guide the fluid management. For fluid refractory and vasopressor-dependent shock, adrenal insufficiency should be considered. Supplemental therapies include blood transfusion, sedation/analgesia while ventilated, optimized oxygenation and ventilation. In those suspected of having immunoglobulin deficiency one can give IV immunoglobulin.

Therapeutic endpoints are as follows:
Clinical:
Heart Rate normalized for age
Capillary refill <2 sec
Normal pulse quality
No difference in central and peripheral pulses
Warm extremities
Blood pressure normal for age
Urine output >1 mL/kg/h
Normal mental status
CVP>8 mmHg
Laboratory:
Decreasing lactate
SvO2>70%

B. Systemic Inflammatory Response Syndrome

Systemic inflammatory response syndrome (SIRS) is an inflammatory state affecting the whole body, frequently a response of the immune system to infection, but not necessarily so. It is related to sepsis, a condition in which individuals both meet criteria for SIRS and have an infection. SIRS may lead to sepsis, severe sepsis and then septic shock which is a serious condition related to systemic inflammation, organ dysfunction, and organ failure. It is a subset of cytokine storm, in which there is abnormal regulation of various cytokines. SIRS is closely related to sepsis, in which patients satisfy criteria for SIRS and have a suspected or proven infection.

Criteria for SIRS were established in 1992 as part of the American College of Chest Physicians/Society of Critical Care Medicine Consensus Conference. The conference concluded that the manifestations of SIRS include, but are not limited to:

body temperature less than 36° C. (96.8° F.) or greater than 38° C. (100.4° F.);

heart rate greater than 90 beats per minute;

tachypnea (high respiratory rate), with greater than 20 breaths per minute; or, an arterial partial pressure of carbon dioxide less than 4.3 kPa (32 mmHg); and white blood cell count less than 4000 cells/mm$^3$ ($4 \times 10^9$ cells/L) or greater than 12,000 cells/mm$^3$ ($12 \times 10^9$ cells/L); or the presence of greater than 10% immature neutrophils (band forms)

SIRS can be diagnosed when two or more of these criteria are present.

Fever and leukocytosis are features of the acute-phase reaction, while tachycardia is often the initial sign of hemodynamic compromise. Tachypnea may be related to the increased metabolic stress due to infection and inflammation, but may also be an ominous sign of inadequate perfusion resulting in the onset of anaerobic cellular metabolism.

In children, the SIRS criteria are modified in the following fashion:

heart rate is greater than 2 standard deviations above normal for age in the absence of stimuli such as pain and drug administration, or unexplained persistent elevation for greater than 30 minutes to 4 hours. In infants, it also includes a heart rate less than the 10th percentile for age in the absence of vagal stimuli, beta-blockers, or congenital heart disease or unexplained persistent depression for greater than 30 minutes;

body temperature obtained orally, rectally, from Foley catheter probe, or from central venous catheter probe less than 36° C. or greater than 38.5° C. (temperature must be abnormal to qualify as SIRS in pediatric patients);

respiratory rate greater than 2 standard deviations above normal for age or the requirement for mechanical ventilation not related to neuromuscular disease or the administration of anesthesia; and white blood count elevated or depressed for age not related to chemotherapy, or greater than 10% bands plus other immature forms.

SIRS criteria are very non-specific, and must be interpreted carefully within the clinical context. These criteria exist primarily for the purpose of more objectively classifying critically ill patients so that future clinical studies may be more rigorous and more easily reproducible.

As an alternative, when two or more of the systemic inflammatory response syndrome criteria are met without evidence of infection, patients may be diagnosed simply with "SIRS." Patients with SIRS and acute organ dysfunction may be termed "severe SIRS" but this is most commonly seen in sepsis and is called severe sepsis.

The causes of SIRS are broadly classified as infectious or noninfectious. As above, when SIRS is due to an infection, it is considered sepsis. Noninfectious causes of SIRS include trauma, burns, pancreatitis, ischemia, and hemorrhage. Other causes include complications of surgery, adrenal insufficiency, pulmonary embolism, complicated aortic aneurysm, cardiac tamponade, anaphylaxis and drug overdose.

Generally, the treatment for SIRS is directed towards the underlying problem or inciting cause (i.e., adequate fluid replacement for hypovolemia, IVF/NPO for pancreatitis, epinephrine/steroids/diphenhydramine for anaphylaxis). Selenium, glutamine, and eicosapentaenoic acid have been shown to be effective in improving symptoms in some clinical trials. Other antioxidants such as vitamin E may be helpful as well.

SIRS is frequently complicated by failure of one or more organs or organ systems. The complications of SIRS and infection include acute lung injury, acute kidney injury, shock and multiple organ dysfunction syndrome (MODS).

II. Measurement of Metabolic Biomarkers

A. Pediatric Subjects

Pediatric subjects are defined herein a newborn to 11 years of age. Neonates are defined as 1 week to 1 month in age, infants are 1 to less than 2 years of age, toddlers are 2 to less than 6 years of age, and school age is 6-11 years of age.

B. Metabolites

The following table provides average "normal" values for various metabolities of interest in the present invention. These values are not limiting and are provided for guidance only. The skilled artisan, using any given technique, is capable of determining "normal" values by running control assays or by referencing published standards, such as at the world-wide-web at serummetabolome.ca:

TABLE 0

Representative Metabolite "Normal" Levels

| Compound | Concentration (µM) |
|---|---|
| 2-Aminobutyrate | 8.2 |
| 2-Hydroxybutyrate | 17.9 |
| 2-Hydroxyisobutyrate | 1.3 |
| 2-Hydroxyisovalerate | 2.7 |
| 2-Methylglutarate | 3.6 |
| 2-Oxoglutarate | 2.6 |
| 2-Oxoisocaproate | 2.6 |
| 3-Hydroxybutyrate | 150.6 |
| 3-Hydroxyisovalerate | 0.9 |
| 3-Methyl-2-oxovalerate | 3.8 |
| Acetate | 119.2 |
| Acetone | 36.7 |
| Adipate | 4.6 |
| Alanine | 157.5 |
| Arginine | 12.9 |
| Asparagine | 14.6 |
| Aspartate | 26.4 |
| Betaine | 13.2 |
| Carnitine | 11.9 |
| Choline | 10.7 |
| Citrate | 54.6 |
| Creatine | 25.6 |
| Creatine phosphate | 5.6 |
| Creatinine | 6.0 |
| Dimethyl sulfone | 2.5 |
| Ethanol | 5.0 |
| Formate | 17.7 |
| Glucose | 584.8 |
| Glutamate | 93.5 |
| Glutamine | 112.8 |
| Glycerol | 353.1 |
| Glycine | 156.2 |
| Histidine | 28.0 |
| Hypoxanthine | 71.8 |
| Isobutyrate | 6.0 |
| Isoleucine | 27.5 |
| Isopropanol | 2.6 |
| Lactate | 2945.5 |
| Leucine | 47.7 |
| Lysine | 55.5 |
| Methanol | 22.1 |
| Methionine | 11.4 |
| O-Acetylcarnitine | 2.8 |
| Ornithine | 34.4 |
| Phenylalanine | 28.6 |
| Proline | 57.4 |

TABLE 0-continued

Representative Metabolite "Normal" Levels

| Compound | Concentration (µM) |
|---|---|
| Propylene Glycol | 99.6 |
| Pyroglutamate | 31.8 |
| Pyruvate | 61.2 |
| Serine | 72.8 |
| Suberate | 34.1 |
| Taurine | 70.4 |
| Threonine | 45.3 |
| Trimethylamine N-oxide | 2.0 |
| Tyrosine | 27.2 |
| Urea | 837.5 |
| Valine | 79.9 |
| myo-Inositol | 9.9 |

C. Samples

As described herein, this inventor relates to methods and materials for assessing metabolites from serum. More particularly, this document relates to the use of metabolite biomarkers for pediatric septic shock and prognosing mortality. As described herein, the levels of one or more of the biomarkers selected from those set forth in Tables 2-3, below, and FIGS. 8A-B. Any combination of the biomarkers listed can be used. For example, the methods can determine the level of one or more, e.g., two or more, three or more, four or more, five or more, six or more, seven or more, eight, nine, ten, or all of the biomarkers listed in Tables 2-3 or FIGS. 8A-B; and comparing the levels of the biomarkers with reference levels of the same biomarkers. The level(s) of the biomarkers may be compared to a reference, wherein the levels of the biomarkers in comparison to the reference is indicative of disease and may be used for prognosis in septic shock.

A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. A "reference level" may also be a "standard curve reference level" based on the levels of one or more biomarkers determined from a population and plotted on appropriate axes to produce a reference curve (e.g., a standard probability curve). Reference levels may also be tailored to specific techniques that are used to measure levels of biomarkers in biological samples, where the levels of biomarkers may differ based on the specific technique that is used.

In some cases, the reference comprises predetermined values for a plurality of biomarkers (e.g., each of the plurality of biomarkers). The predetermined value can take a variety of forms. It can be a level of a biomarker in a control subject (e.g., a subject with a particular disease). A predetermined value that represents a level(s) of a biomarker referred to herein as a predetermined level. A predetermined level can be single cut-off value, such as a median or mean. It can be a range of cut-off (or threshold) values, such as a confidence interval.

Subjects associated with predetermined values are typically referred to as controls. A control subject may or may not have disease. Thus, in some cases the level of a biomarker in a subject being greater than or equal to the level of the biomarker in a control subject is indicative of a clinical status. In other cases the level of a biomarker in a subject being less than or equal to the level of the biomarker in a control subject is indicative of clinical status. The amount of the greater than and the amount of the less than is usually of a sufficient magnitude to, for example, facilitate distinguishing a subject from a control subject using the disclosed methods. Typically, the greater than, or the less than, that is sufficient to distinguish a subject from a subject mammal is a statistically significant greater than, or a statistically significant less than. In cases where the level of a biomarker in a subject being equal to the level of the biomarker in a control subject is indicative of a clinical status, the "being equal" refers to being approximately equal (e.g., not statistically different).

The predetermined value can depend upon a particular population of subject selected. For example, an apparently healthy population will have a different 'normal' range of biomarkers than will a population of subjects which have, or are likely to have, disease. Accordingly, the predetermined values selected may take into account the category (e.g., healthy, at risk, diseased) in which a subject falls. Appropriate ranges and categories can be selected with no more than routine experimentation by those of ordinary skill in the art.

In some cases a predetermined value of a biomarker is a value that is the average for a population of healthy subjects (e.g., human subjects who have no apparent signs and symptoms of any disease). The predetermined value will depend, of course, on the particular biomarker selected and even upon the characteristics of the population in which the subject lies.

D. $^1$H NMR Spectroscopy

Proton NMR (also Hydrogen-1 NMR, or $^1$H NMR) is the application of nuclear magnetic resonance in NMR spectroscopy with respect to hydrogen-1 nuclei within the molecules of a substance, in order to determine the structure of its molecules. In samples where natural hydrogen (H) is used, practically all of the hydrogen consists of the isotope 1H (hydrogen-1; i.e., having a proton for a nucleus). A full $^1$H atom is called protium.

Simple NMR spectra are recorded in solution, and solvent protons must not be allowed to interfere. Deuterated (deuterium=$^2$H, often symbolized as D) solvents especially for use in NMR are preferred, e.g., deuterated water, D2O, deuterated acetone, $(CD_3)_2CO$, deuterated methanol, $CD_3OD$, deuterated dimethyl sulfoxide, $(CD_3)2SO$, and deuterated chloroform, $CDCl_3$. However, a solvent without hydrogen, such as carbon tetrachloride, $CCl_4$ or carbon disulphide, $CS_2$, may also be used.

Historically, deuterated solvents were supplied with a small amount (typically 0.1%) of tetramethylsilane (TMS) as an internal standard for calibrating the chemical shifts of each analyte proton. TMS is a tetrahedral molecule, with all protons being chemically equivalent, giving one single signal, used to define a chemical shift=0 ppm. It is volatile, making sample recovery easy as well. Modern spectrometers are able to reference spectra based on the residual proton in the solvent (e.g., the CHCl3, 0.01% in 99.99% $CDCl_3$). Deuterated solvents are now commonly supplied without TMS.

Deuterated solvents permit the use of deuterium frequency-field lock (also known as deuterium lock or field lock) to offset the effect of the natural drift of the NMR's magnetic field. In order to provide deuterium lock, the NMR constantly monitors the deuterium signal resonance frequency from the solvent and makes changes to keep the resonance frequency constant. Additionally, the deuterium signal may be used to accurately define 0 ppm as the resonant frequency of the lock solvent and the difference between the lock solvent and 0 ppm (TMS) are well known.

Proton NMR spectra of most organic compounds are characterized by chemical shifts in the range +14 to −4 ppm and by spin-spin coupling between protons. The integration curve for each proton reflects the abundance of the individual protons. Simple molecules have simple spectra. The spectrum of ethyl chloride consists of a triplet at 1.5 ppm and a quartet at 3.5 ppm in a 3:2 ratio. The spectrum of benzene consists of a single peak at 7.2 ppm due to the diamagnetic ring current.

Chemical shift values, symbolized by δ, are not precise, but typical—they are to be therefore regarded mainly as orientational. Deviations are in ±0.2 ppm range, sometimes more. The exact value of chemical shift depends on molecular structure and the solvent in which the spectrum is being recorded. Hydrogen nuclei are sensitive to the hybridization of the atom to which the hydrogen atom is attached and to electronic effects. Nuclei tend to be deshielded by groups which withdraw electron density. Deshielded nuclei resonate at higher δ values, whereas shielded nuclei resonate at lower δ values.

Examples of electron withdrawing substituents are —OH, —OCOR, —OR, —$NO_2$ and halogens. These cause a downfield shift of approximately 2-4 ppm for H atoms on Cα and of less than 1-2 ppm for H atoms on Cβ. Cα is an aliphatic C atom directly bonded to the substituent in question, and Cβ is an aliphatic C atom bonded to Cα. Carbonyl groups, olefinic fragments and aromatic rings contribute sp2 hybridized carbon atoms to an aliphatic chain. This causes a downfield shift of 1-2 ppm at Cα.

Note that labile protons (—OH, —$NH_2$, —SH) have no characteristic chemical shift. However such resonances can be identified by the disappearance of a peak when reacted with $D_2O$, as deuterium will replace a protium atom. This method is called a $D_2O$ shake. Acidic protons may also be suppressed when a solvent containing acidic deuterium ions (e.g., methanol-d4) is used.

The chemical shift is not the only indicator used to assign a molecule. Because nuclei themselves possess a small magnetic field, they influence each other, changing the energy and hence frequency of nearby nuclei as they resonate—this is known as spin-spin coupling. The most important type in basic NMR is scalar coupling. This interaction between two nuclei occurs through chemical bonds, and can typically be seen up to three bonds away.

The effect of scalar coupling can be understood by examination of a proton that has a signal at 1 ppm. This proton is in a hypothetical molecule where three bonds away exists another proton (in a CH—CH group for instance), the neighboring group (a magnetic field) causes the signal at 1 ppm to split into two, with one peak being a few hertz higher than 1 ppm and the other peak being the same number of hertz lower than 1 ppm. These peaks each have half the area of the former singlet peak. The magnitude of this splitting (difference in frequency between peaks) is known as the coupling constant. A typical coupling constant value would be 7 Hz.

The coupling constant is independent of magnetic field strength because it is caused by the magnetic field of another nucleus, not the spectrometer magnet. Therefore it is quoted in hertz (frequency) and not ppm (chemical shift).

In another molecule a proton resonates at 2.5 ppm and that proton would also be split into two by the proton at 1 ppm. Because the magnitude of interaction is the same the splitting would have the same coupling constant 7 Hz apart. The spectrum would have two signals, each being a doublet. Each doublet will have the same area because both doublets are produced by one proton each.

III. Kits

The document also provides kits for evaluating biomarkers in a mammal. The kits of the invention can take on a variety of forms. Typically, the kits will include reagents suitable for determining levels of one or more of the biomarkers disclosed herein. For example, the kits may contain one or more control samples. For example, the control samples can be specific for levels of one or more biomarkers that correspond to various forms of disease. Typically, a comparison between the levels of the biomarkers in the sample from the mammal and the levels of the biomarkers in the control samples is indicative of a clinical status.

Also, the kits, in some cases, will include written information (indicia) providing a reference (e.g., predetermined values), wherein a comparison between the levels of the biomarkers in the subject and the reference (pre-determined values) is indicative of a clinical status. In some cases, the kits comprise software useful for comparing biomarker levels with a reference (e.g., a prediction model). Usually the software will be provided in a computer readable format such as a compact disc, but it also may be available for downloading via the internet. However, the kits are not so limited and other variations will be apparent to one of ordinary skill in the art.

IV. Examples

The following examples are included to demonstrate particular embodiments of the invention. It should be appreciated by those of skill in the art that the techniques disclosed in the examples that follow represent techniques discovered by the inventor to function well in the practice of the invention. However, those of skill in the art, should in light of the present disclosure, appreciate that many changes can be made in the specific embodiments which are disclosed and still obtain a like or similar result without departing from the spirit and scope of the invention.

Example 1

Methods

Metabolite Sample Preparation.

All 140 serum samples (200 µl) were thawed and filtered twice using 3 kDa NanoSep microcentrifuge filters which were initially prewashed five times with distilled and deionized water to reduce preservative contamination. Filtered proteins were rinsed using an additional 100 µl of $D_2O$. Filtrates (the final sample volume ranged from 150 to 250 µl) were then transferred to clean microfuge tubes. Samples were brought to 400 µl by the addition of 80 µl of phosphate buffer (0.5 M $NaH_2PO_4$ buffer solution at pH 7.0) containing 2.5 mM 2,2-dimethyl-2-silapentane-5-sulfonate (DSS, final concentration 0.5 mM), 10 µl of sodium azide (1 M $NaN_3$) to limit bacterial growth, and $D_2O$. The final concentration of DSS (0.5 mM for each sample) was used as an internal standard. The pH of the samples was adjusted to 7.00±0.04. A total of 58 metabolites were identified and quantifies for each of the three cohorts, septic shock, SIRS/ICU controls and healthy controls. The analysis was performed on these 58 metabolites unless otherwise stated.

NMR Spectroscopy and Metabolite Concentration Profiling.

For the protocol of samples' preparation see the online data supplement. NMR spectra were obtained on a Bruker AVANCE 600 MHz spectrometer (Bruker BioSpin Ltd., Canada) using a standard Bruker 1D spectroscopy presaturation pulse sequence (noesypr1d) with mixing time of 100 ms [20, 25]. The concentration of 4,4-dimethyl-4-silapentane-1-sulfonic acid (DSS) was used as a reference to determine metabolite concentrations during targeted profiling [20] (Chenomx NMR Suite 7.1, Chenomx Inc., Canada). Each concentration was normalized to the total sum of concentrations, excluding the two highest concentrated metabolites: lactate and glucose, which otherwise would dominate the normalization [20, 26].

Statistical Modeling.

Normalized concentrations were used for multivariate analysis (SIMCA-P+ 12.0.1, Umetrics, Sweden). The PCA model was designed to identify and exclude outliers before PLS-DA models construction with class ID (healthy control, SIRS/ICU control, septic shock). To evaluate the PLS-DA model, R2Y and Q2 metrics were calculated using a sevenfold cross-validation method [27]. R2Y metric describes the percentage of variation explained by the model; Q2 shows the predictive ability of the model. The difference between these metrics describes the model's goodness-of-fit. Next, the OPLS-DA method was applied to models including only two classes: septic shock vs. healthy, SIRS/ICU controls vs. healthy and septic shock vs. SIRS/ICU controls within all subjects and specific age groups (infants, toddlers, school age). Additionally, two OPLS-DA models were constructed to reveal mortality factors utilizing: 1) 20 septic shock samples (10 non-survivors and 10 age-gender-matched controls) and 2) 23 patients with complicated course (10 non-survivors and 13 survivors). The OPLS-DA method for age groups and mortality models was based on potentially relevant metabolites selected in 2-sample t-tests with $p<0.2$ as a threshold. For each OPLS-DA model the area under a receiver operator curve (AUROC) was calculated (Metz ROC Software, USA) [28]. The sensitivity, specificity and accuracy were determined on the basis of sample class prediction during sevenfold cross-validation (Y-predcv) in SIMCA-P+ software. The results of ROC analysis were then compared to the predictive values of procalcitonin (PCT) levels and to the Pediatric Risk of Mortality III-Acute Physiology Scores (PRISM III-APS) collected for the enrolled patients.

Data Collection.

The study protocol was approved by the Institutional Review Boards of each of the 11 participating institutions. The data collection protocol has been previously described in detail [50]. Briefly, children <11 years of age admitted to a pediatric intensive care unit (PICU) and meeting pediatric—specific criteria for SIRS or septic shock were eligible [51]. Controls were recruited from the ambulatory departments of participating institutions using previously published inclusion and exclusion criteria [50]. Clinical care was not directed by the study and, except when informed consent could not be obtained, no child was excluded. After informed consent from parents or legal guardians and within 24 hours of admission to the PICU, serum samples were obtained. Annotated clinical and laboratory data were collected daily while the participant was in the PICU Illness severity was calculated using the PRISM III—APS (Pediatric Risk of Mortality III—Acute Physiology) score [52]. Organ failure was defined using pediatric—specific criteria and tracked up to the first 7 days of PICU admission [51]. Septic shock patients with persistence of 2 or more than 2 organ failures at 7 days after study enrollment were specified as patients with complicated course (adapted from [53]). Mortality was tracked for 28 days after enrollment.

For the septic shock patients, all samples were drawn from existing arterial catheters or central venous catheters within 24 h of diagnosis of septic shock. For the SIRS/ICU controls all samples were drawn from existing arterial catheters or central venous catheters within 24 h of admission to PICU. For the healthy controls, all samples were drawn at the time of a scheduled phlebotomy. All samples were immediately spun down, the serum isolated, and placed in a −80° C. freezer. None of the samples that were provided for metabolomics analysis had undergone a previous freeze/thaw cycle.

Example 2

Results

Predictive Models of all Subjects.

Figure 1:
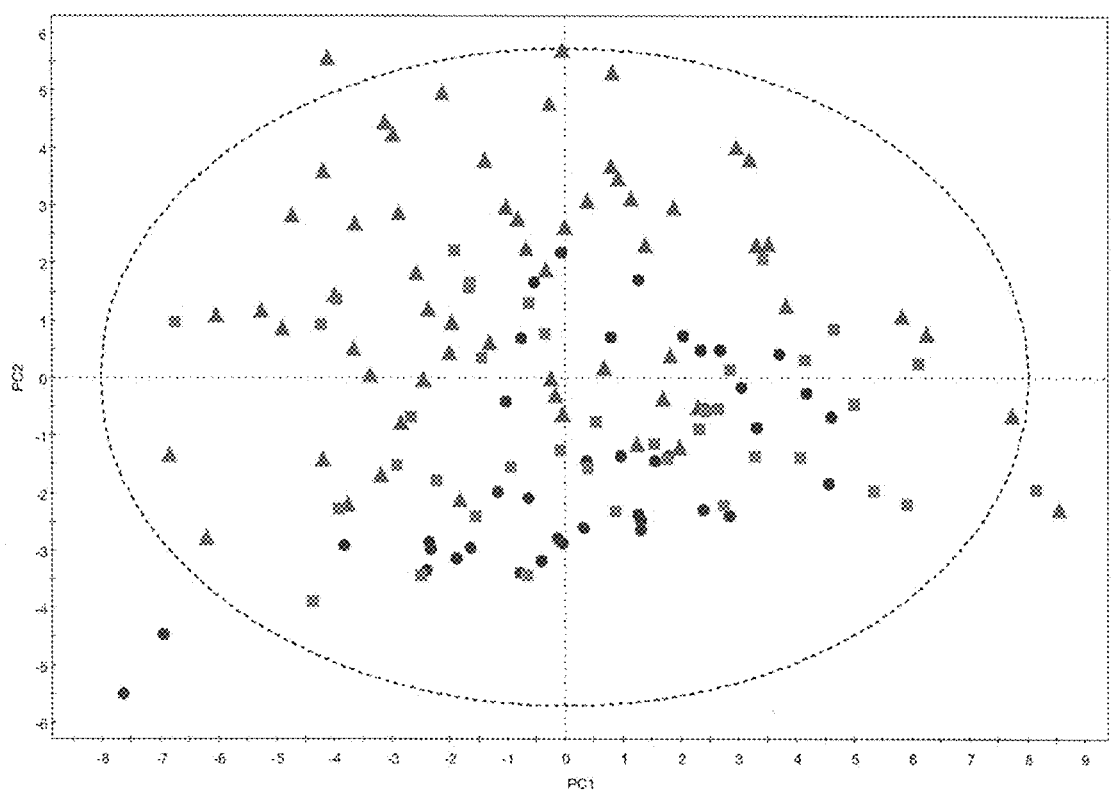
FIG. 1. A score scatter plot of the first two PCA principal components (PC1 and PC2). The PCA model summarizes the variation in the data set of septic shock samples (triangles), SIRS/ICU controls (squares) and healthy controls (dots) and highlights outliers. Five samples (2 septic shock samples, 1 SIRS/ICU control and 2 healthy controls) are placed outside the ellipse that describes 95% confidence interval of the Hotelling's T-squared distribution.
Figure 2:
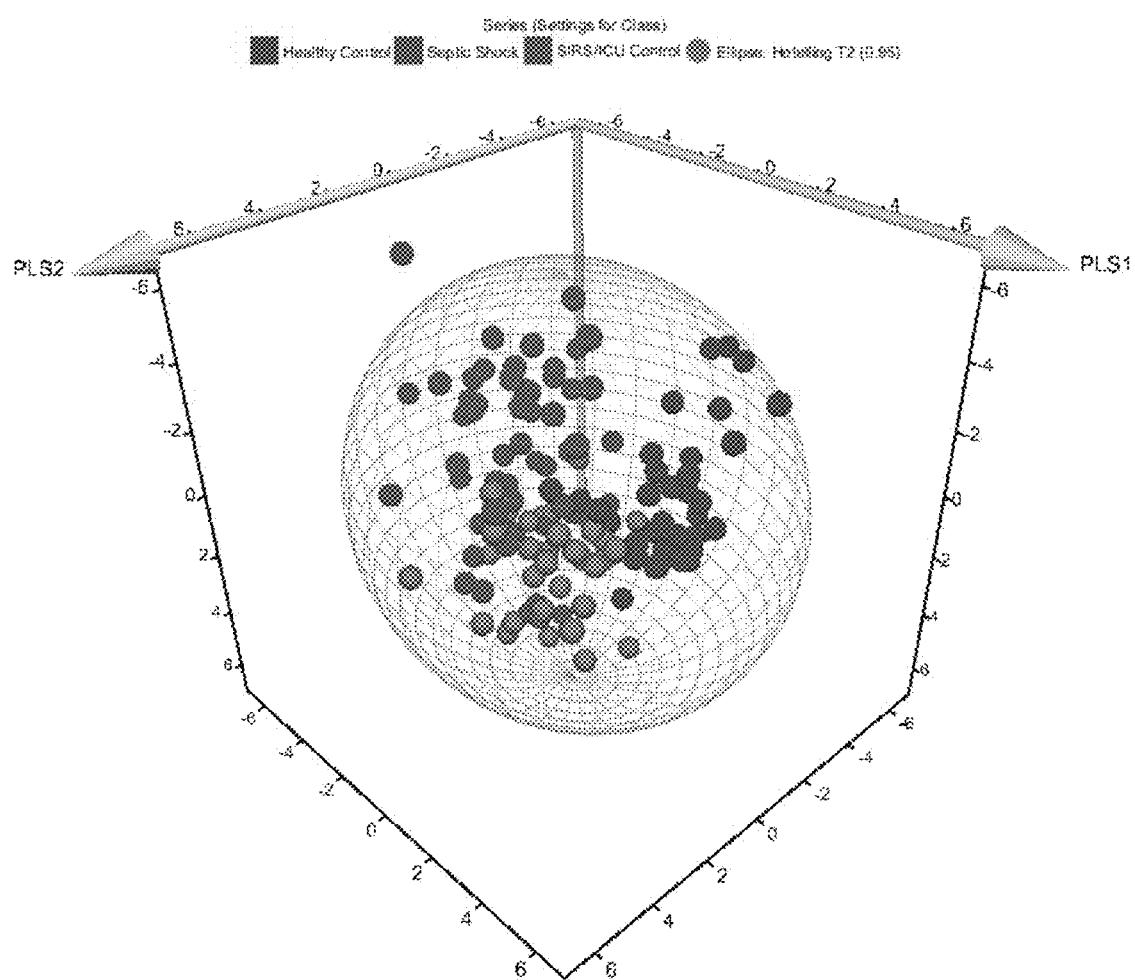
FIG. 2. The 3D PLS-DA score scatter plot for septic shock patients (red), SIRS/ICU controls (green) and healthy controls (blue). Studied groups are well clustered and distinguished along three PLS components. The sphere describes 95% confidence interval of the Hotelling's T-squared distribution.
Figure 2:
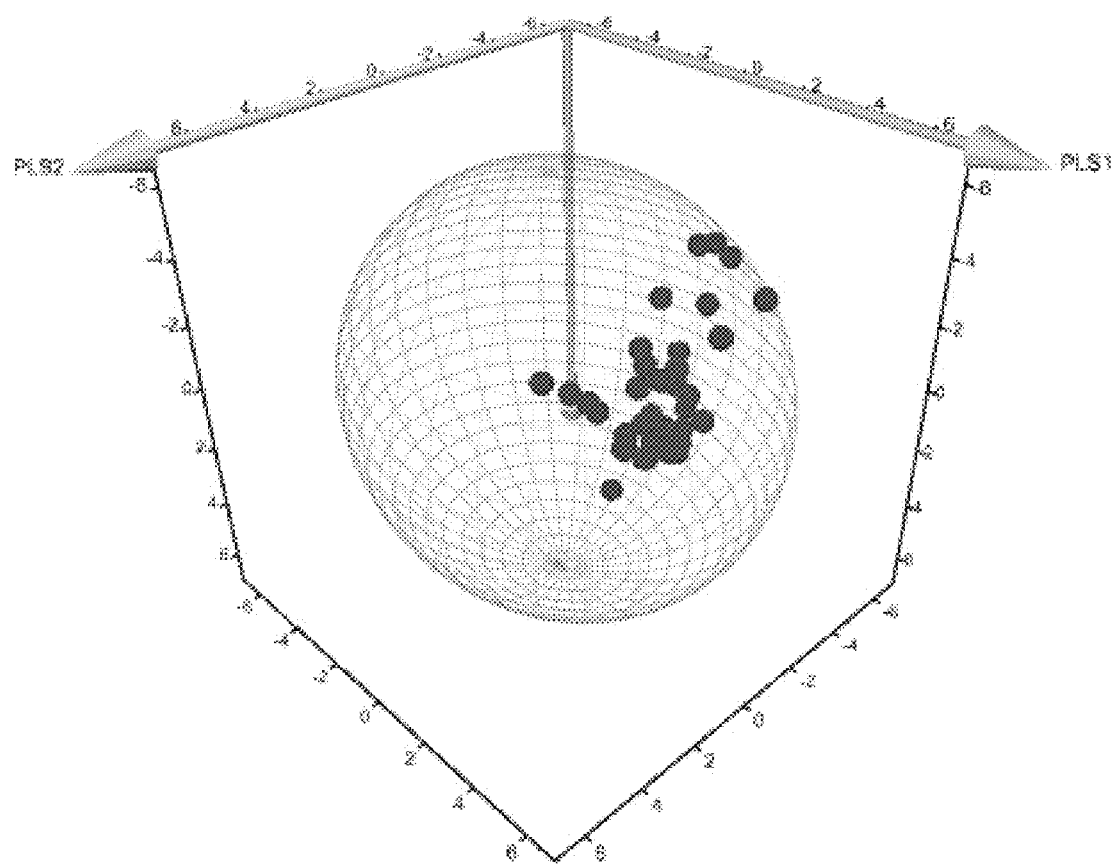
Figure 2:
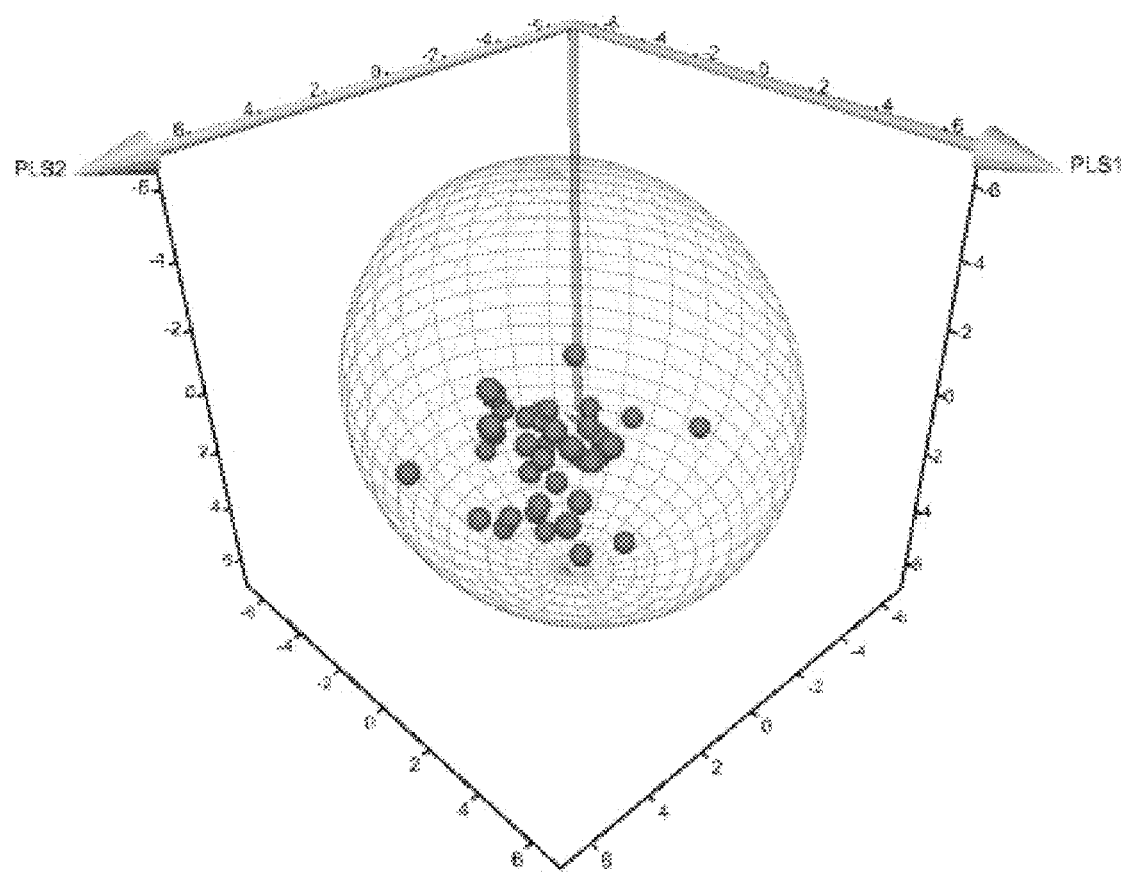
Figure 2:
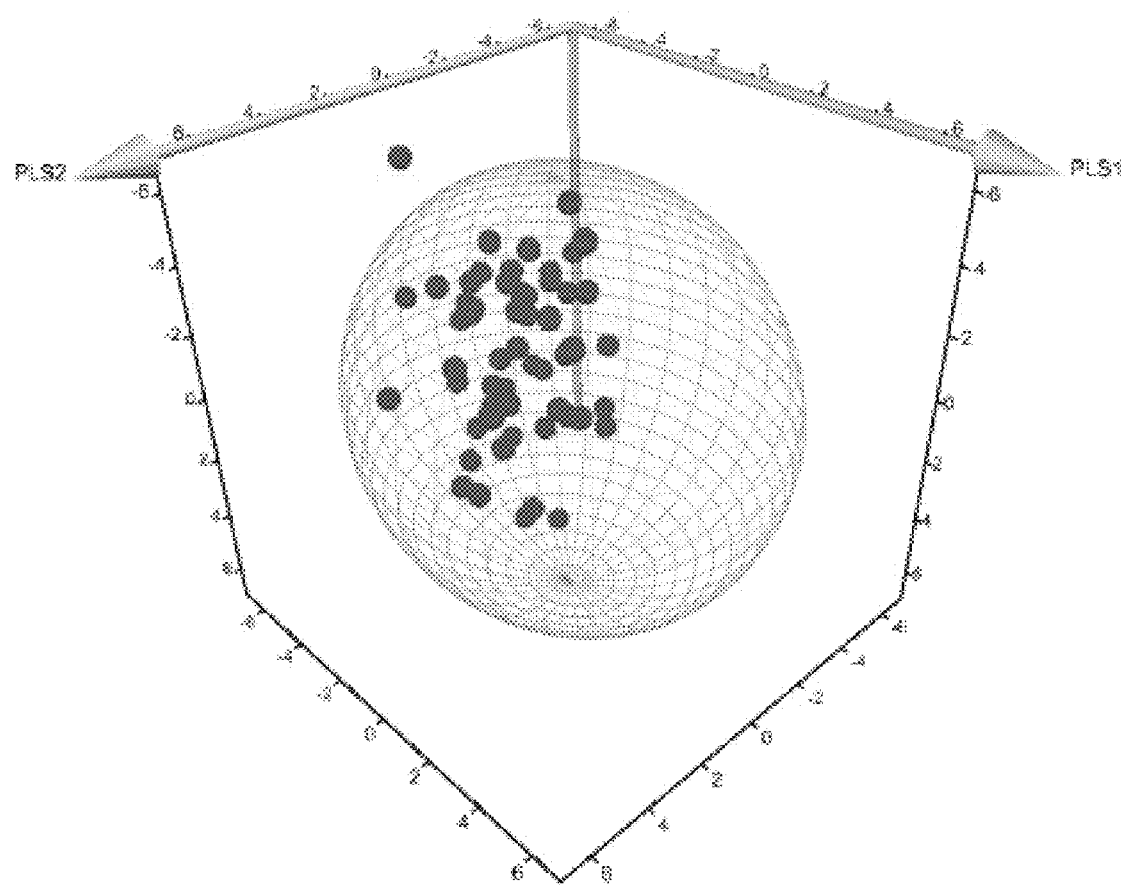

The PCA model identified five outliers: 2 healthy controls (infant and toddler), 1 SIRS/ICU control (school age) and 2 septic shock samples (toddler and school age). The samples were placed outside the 95% confidence interval of the Hotelling's T-squared distribution in the score scatter plot (FIG. 1). Outliers might seriously disturb a model therefore for all subsequent steps of statistical analysis these outliers were excluded. Based on the PCA results showing sample grouping a supervised PLS-DA analysis was performed to reveal specific metabolic changes in defined groups and improve the separation between specimens. Three PLS components were used to build the model and the results are presented by three-dimensional score scatter plots (FIG. 2). The scores of healthy controls are visibly distinguished from SIRS/ICU controls and septic shock samples indicating specific differences in metabolic profiles of the subjects. Patient groups are well clustered and the R2Y and Q2 metrics are 0.48 and 0.35, respectively. Despite the fact that some of SIRS/ICU controls and septic shock specimens do overlap, which may result from similar biological responses of these cases, the PLS-DA model appears to be highly relevant. In this model there is a visible tendency reflecting separation of patient groups that is in agreement with the morbidity and severity of septic shock. The disease reveals a very specific metabolic response in a child's body that is much stronger than other parameters such as age and gender. When the inventors applied statistical methods to distinguish all studied specimens according to age or gender the results revealed poor models whose patterns could not be fitted. Moreover, a direct comparison between age categories within one patient class (healthy, SIRS/ICU controls or septic shock) did not represent any significant separation indicating that changes in metabolism of studied individuals were mainly associated with health condition rather than with age or gender.

Figure 5A:
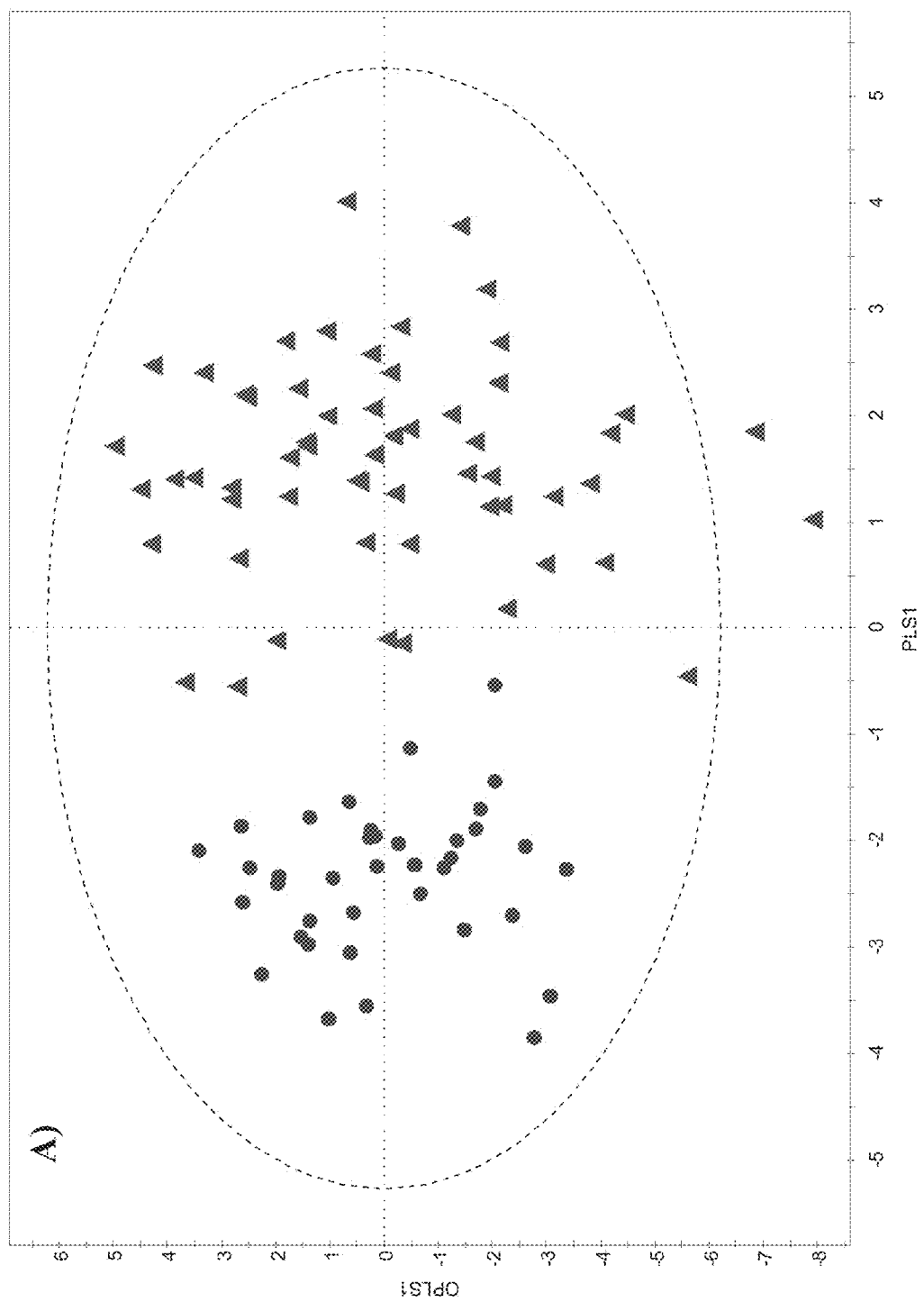
Figure 5C:
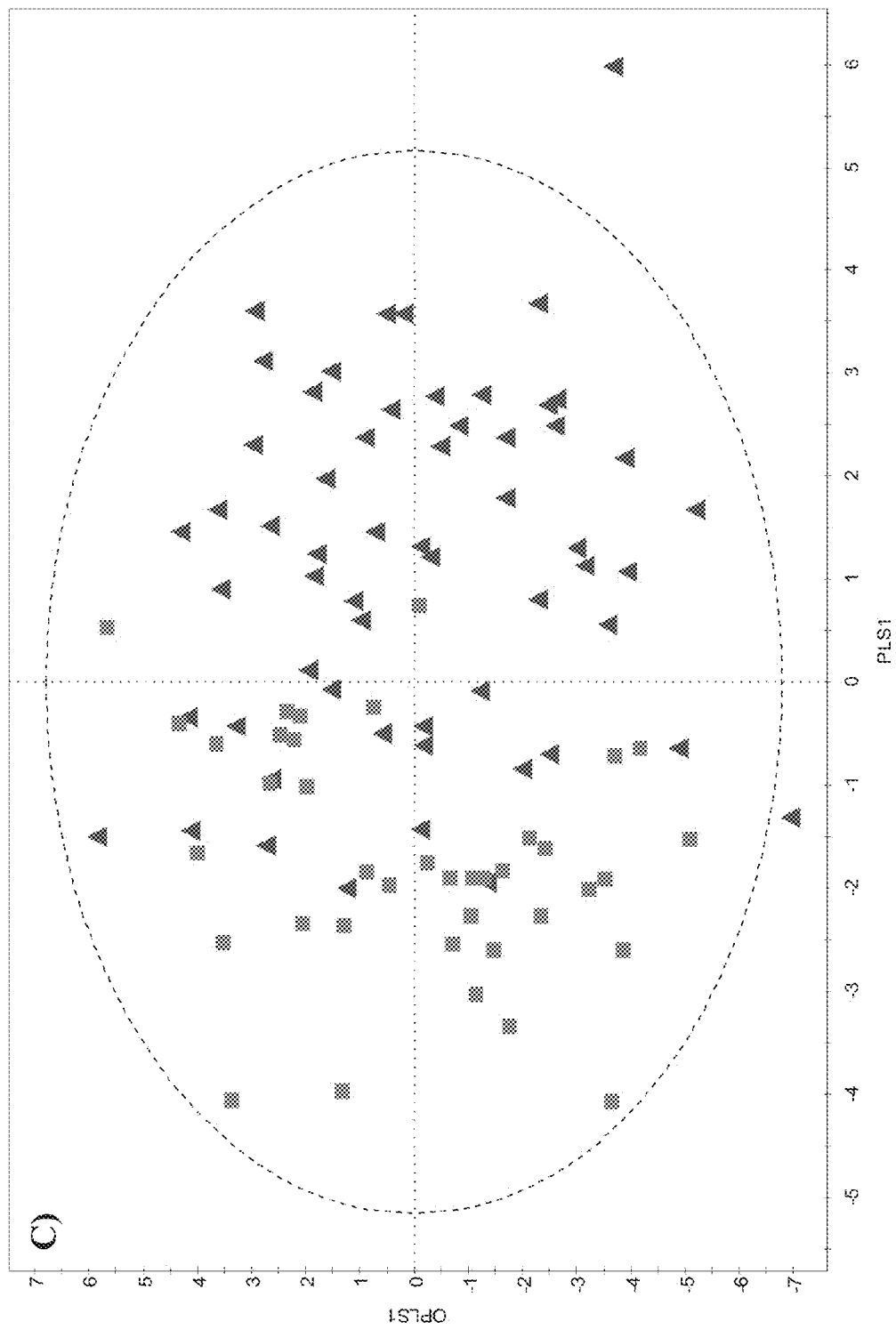

Additionally, an OPLS-DA method was applied to compare metabolic variance in patient groups consisting of only two classes: septic shock and healthy subjects, SIRS/ICU and healthy controls, septic shock and SIRS/ICU controls. The score scatter plots for each statistical analysis are presented in FIGS. 5A-C (online data supplement). Both OPLS-DA models: SIRS/ICU patients vs. healthy controls (FIG. 5A) and septic shock vs. healthy controls (FIG. 5B) show clear separation of groups and are described by high values of R2Y and Q2 parameters that indicate powerful and reliable models. The scores of the OPLS-DA model that contains septic shock patients and SIRS/ICU controls (FIG. 5C) are not as well distinguished as the scores in the previous plots. However, there is a visible tendency that allows for clustering septic shock specimens and SIRS/ICU controls along the first PLS component. The calculated validation metrics and AUROC for each model are summarized in Table 2.

Predictive Models of Age Groups.

It has been reported that clinical parameters used to define SIRS, organ dysfunction and sepsis are strongly affected by the age of pediatric patients [29]. The inventors tested this relationship by designing OPLS-DA models for the specific age groups: infants, toddlers and school age (Table 1). Neonates were not considered because of a small number of available samples (n=7). The results are presented in Table 2 and the score scatter plots are shown in FIG. 3. It is noted that the models obtained for SIRS/ICU controls vs. healthy, septic shock vs. healthy and septic shock vs. SIRS/ICU controls are quite similar between infants and toddlers. Validation metrics R2Y and Q2 are also comparable within these two age categories. The score scatter plots (FIG. 3) show very clear separation between SIRS/ICU patients and healthy controls and between septic shock specimens and healthy controls for infants and toddlers. Moreover, these models are described by high values of R2Y, Q2 and ROC parameters (Table 2), confirming their great strengths. The score scatter plots of septic shock patients and SIRS/ICU controls for infants and toddlers are not so well distinguished and some of the samples are overlapping, however, these OPLS-DA models are still more powerful and reliable (higher values of R2Y and Q2 metrics) than the model constructed for all subjects. Interestingly, the school age samples represent much different metabolic behavior than younger children. Unlike infants and toddlers, the scores plot of the OPLS-DA model for SIRS/ICU patients vs. healthy controls sample data are converged almost in the same region and validation parameters calculated for this model have low values, R2Y=0.42 and Q2=0.28. Nonetheless, the OPLS-DA models containing septic shock patients (septic shock specimens vs. healthy controls and septic shock specimens vs. SIRS/ICU controls) demonstrate good separation and are described by reasonable values of R2Y and Q2 metrics.

In order to describe specific biopatterns within OPLS-DA age groups models, the OPLS regression coefficients were calculated and only metabolites with significant changes in concentration ($p<0.05$) were considered (Table 3). As a result, the numbers of the most meaningful metabolites for separation between SIRS/ICU patients and healthy controls include the following: 20 metabolites for infants, 10 for toddlers and 7 for school age children. The metabolic patterns found in the OPLS-DA model consisting of septic shock patients and healthy controls show 10 significant metabolites within infants, 12 within toddlers and 14 for school age patients. Seventeen OPLS regression coefficients (metabolites) appeared to be the most important for differentiating septic shock individuals from SIRS/ICU patients for infants while for toddlers and school age the numbers are 4 and 15, respectively.

Mortality Models.

Figure 6A:
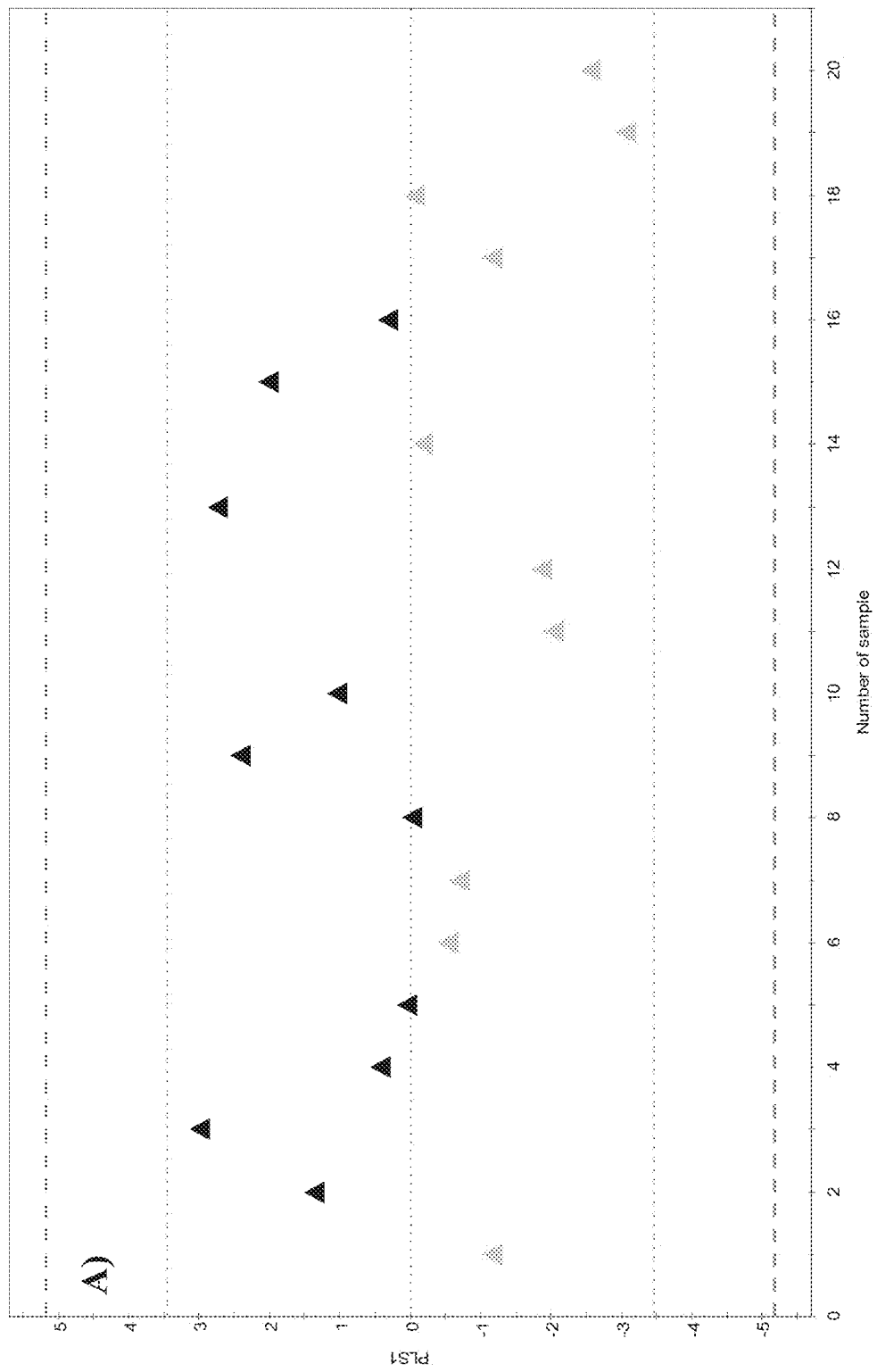
FIGS. 6A-B.
Figure 6B:
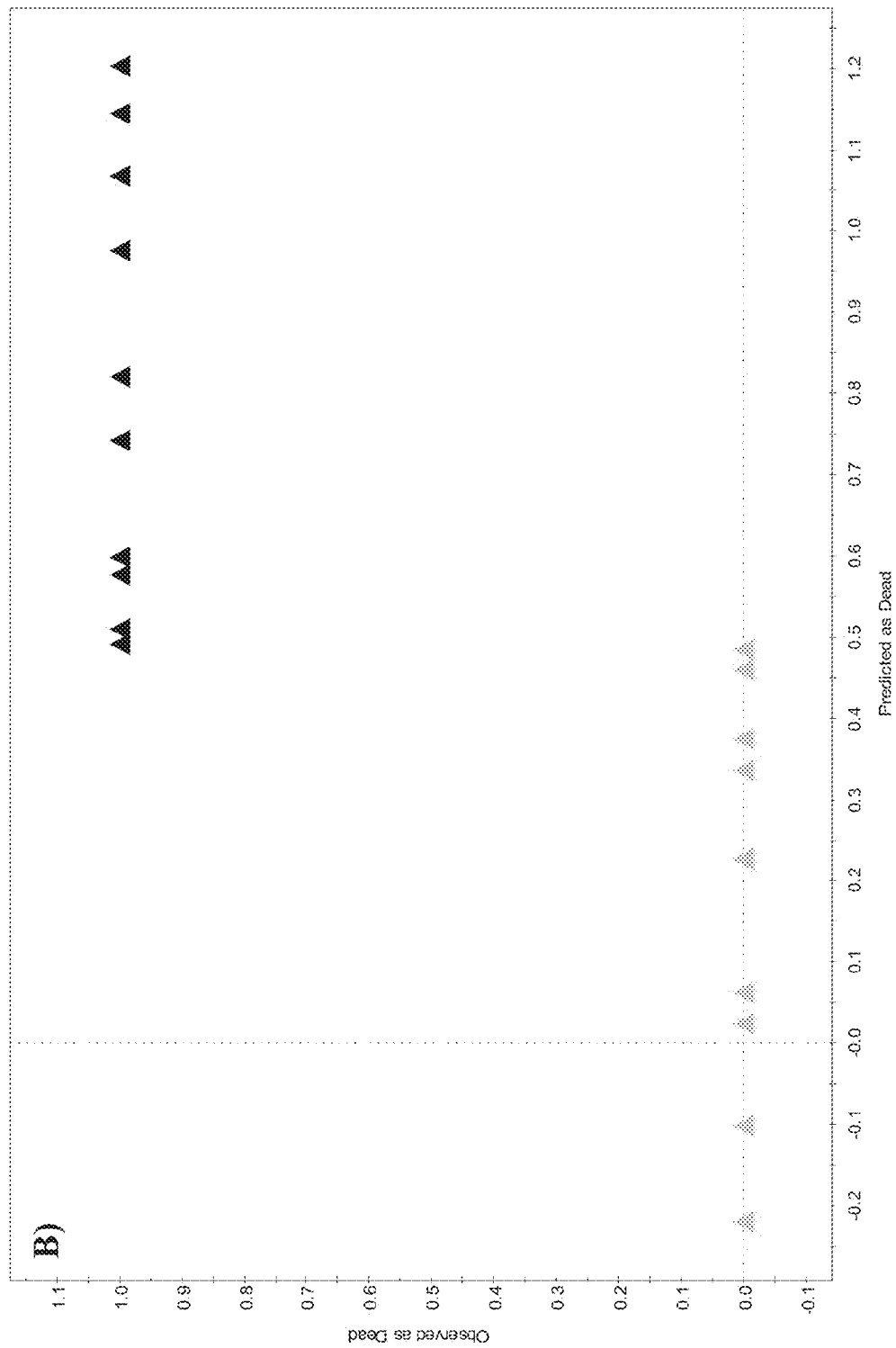
Figure 7A:
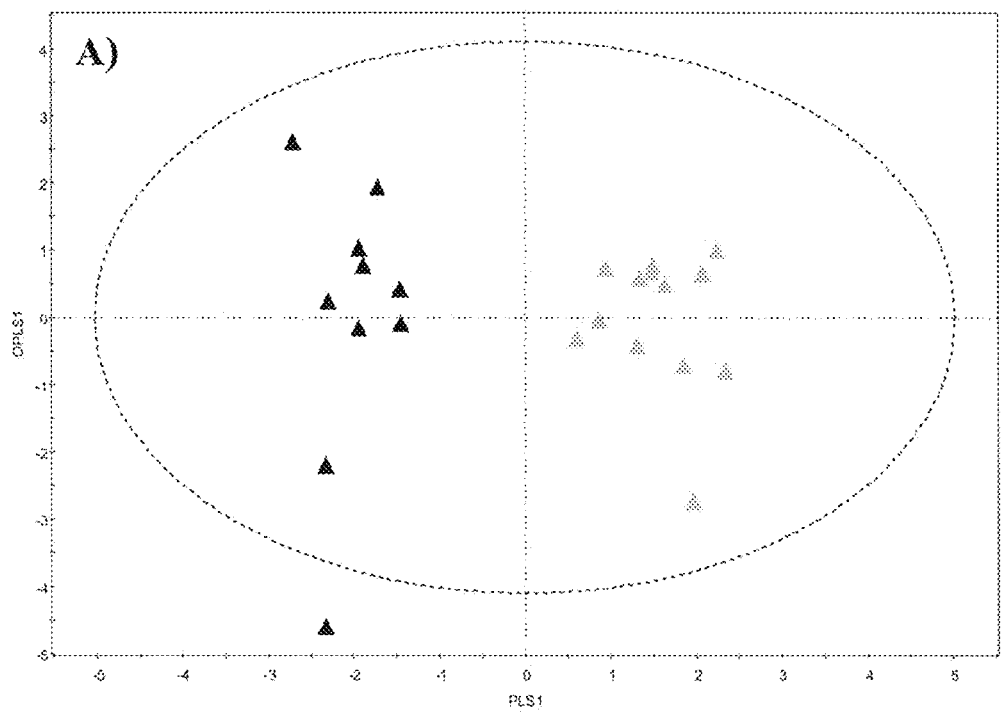
FIGS. 7A-B.
Figure 7B:
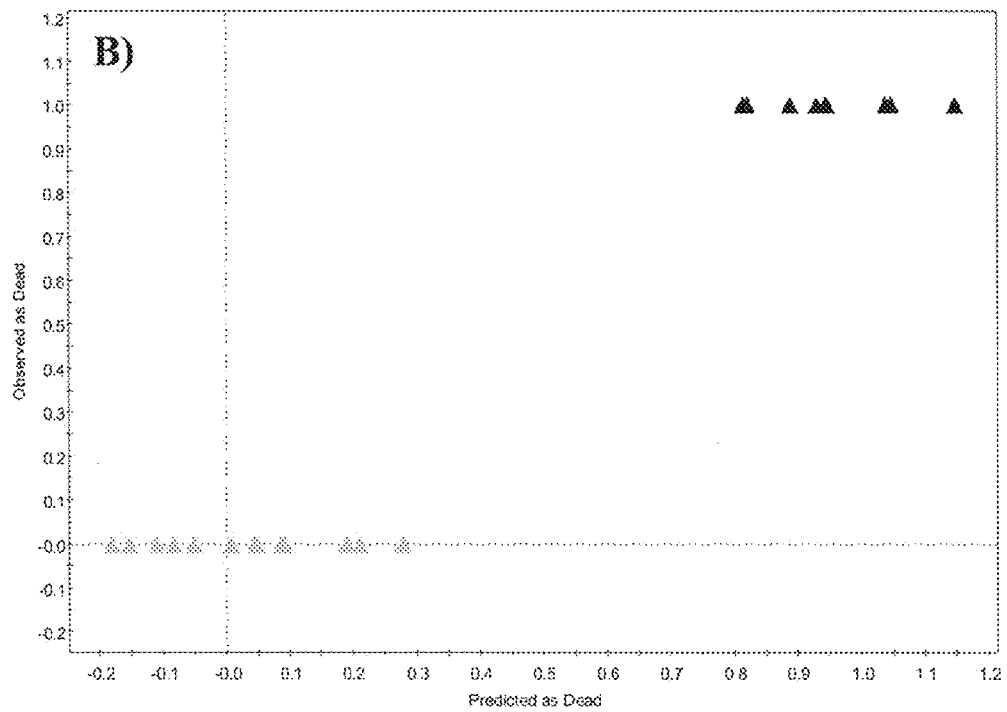

In the first mortality model (10 septic shock non-survivors and 10 age- and gender-matched septic shock survivors), the inventors detected eleven significant metabolites. The OPLS-DA score scatter plot shows good separation between survivors and non-survivors along the first PLS component (FIG. 6A). Although one sample from non-survivors is situated close to the survivor group, none of the studied samples were predicted in the wrong way (FIG. 6B). The calculated R2Y and Q2 metrics were respectively 0.63 and 0.47. The second mortality model was based on the serum samples collected from 23 septic shock patients with a complicated course, i.e., ≥2 organ failures ≥7 days after onset of septic shock (10 non-survivors and 13 survivors). In total eighteen metabolites were selected as potentially important variables. The OPLS-DA modeling method led to clear separation between the two groups of patients with high validation metrics including R2Y=0.93 and Q2=0.82. As it is presented in the score scatter plot non-survivors are very well distinguished from patients who survived (FIG. 7A) and none of non-surviving patients was predicted as a surviving patient in the implemented analysis (FIG. 7B). The calculated AUROC values were 0.91 for the first mortality model and 1.0 for the second model (Table 4).

Comparison with Conventional Predictors for Septic Shock and its Outcome in PICU.

In addition to investigating the use of metabolomics for septic shock diagnosis and outcome prediction in PICU, the inventors compared the results of ROC analysis for metabolomics data and PCT and PRISM III-APS data for the models: septic shock and SIRS/ICU control patients and age- and gender-matched survivors and non-survivors (see Table 5). The AUROC values obtained for septic shock diagnosis are quite similar for all predictors. However, comparing the results calculated for the mortality model, using a metabolomics approach seems to be much more favorable than PCT concentration and PRISM III-APS score in the prognostic evaluation of mortality for septic shock patients in the PICU.

TABLE 1

Demographic and clinical characteristics of enrolled subjects in the study*

|  | Neonates | Infants | Toddlers | School age |
|---|---|---|---|---|
| Age range | 1 wk-1 mo | 1 mo-1 yr | 2-5 yrs | 6-11 yrs |
| Age (years)* | 0.1 | 1 | 3.4 | 8.3 |
|  |  | (0.5-1.4) | (2.4-4.4) | (7.5-9.4) |
| Number of subjects | 7 | 47 | 54 | 32 |
| Males/females (n) | 4/3 | 28/19 | 30/24 | 16/16 |
| Race (n) |  |  |  |  |
| White | 1 | 28 | 34 | 17 |
| Black/African American | 4 | 5 | 2 | 5 |
| Asian | n/a | 2 | 3 | 1 |
| Native Hawaiian/Pacific Islander | n/a | n/a | 1 | n/a |
| Unknown/Unavailable | 2 | 12 | 14 | 9 |
| Number of healthy controls | 0 | 13 | 18 | 9 |
| SIRS/ICU controls |  |  |  |  |
| Number of patients | 2 | 13 | 16 | 9 |
| PRISM III-APS score* | 3.5 | 10 | 8 | 8 |
|  | (3.25-3.75) | (7-11) | (4.5-14) | (6-10) |
| PCT (ng/ml)* | 1.7 | 2.1 | 1.1 | 1.1 |
|  |  | (1.0-2.4) | (0.1-2.4) | (0.1-3.85) |
| Septic shock patients |  |  |  |  |
| Number of patients | 5 | 21 | 20 | 14 |
| Complicated course (n) | 2 | 10 | 7 | 4 |
| Deaths (n) | 1 | 6 | 2 | 1 |
| PRISM III-APS score* | 24 | 17 | 12.5 | 11.5 |
|  | (12-27) | (15-23) | (8-19.8) | (10.3-20.8) |
| PCT (ng/ml)* | 3.3 | 10.3 | 5.7 | 10.7 |
|  | (2.5-4.1) | (2-17.4) | (2.6-25.8) | (5.3-21.4) |
| Number of patients with: |  |  |  |  |
| Gram-+tive bacteria (%) | 2 (40) | 12 (57) | 12 (60) | 4 (29) |
| Gram-neg bacteria (%) | 1 (20) | 8 (38) | 6 (26) | 6 (43) |
| Polimicrobial infctn (%) | n/a | 1 (4) | n/a | n/a |
| Negative cultures (%) | 2 (40) | n/a | 2 (10) | 3 (21) |
| Infection site (n): |  |  |  |  |
| Blood | 3 | 16 | 13 | 7 |
| Lung | n/a | 5 | 5 | 1 |
| Urine | n/a | n/a | n/a | 1 |
| CSF | n/a | n/a | n/a | n/a |

*All children were divided into four age groups according to previously published age-specific categories for sepsis [29].

TABLE 2

Summary of the quality of the results of OPLS-DA models for all serum samples of diagnostic groups and specific age groups**

| OPLS-DA models | Samples | Quality results OPLS-DA | | | | | |
|---|---|---|---|---|---|---|---|
| | | R2Y | Q2 | P value | Sensitivity:Specificity | PPV:NPV | ACC | AUROC |
| SIRS/ICU controls vs. healthy controls | All | 0.74 | 0.6 | $1.56 \times 10^{-13}$ | $0.90 \pm 0.10:0.95 \pm 0.07$ | 0.95:0.90 | 0.92 | 0.95 |
| | Infants | 0.72 | 0.62 | $2.2 \times 10^{-5}$ | $0.92 \pm 0.14:0.92 \pm 0.16$ | 0.92:0.92 | 0.92 | 0.97 |
| | Toddlers | 0.87 | 0.69 | $7.2 \times 10^{-7}$ | $0.94 \pm 0.12:0.88 \pm 0.15$ | 0.88:0.94 | 0.91 | 0.98 |
| | School age | 0.41 | 0.29 | 0.087 | $0.75 \pm 0.30:0.78 \pm 0.27$ | 0.75:0.78 | 0.77 | 0.85 |
| Septic shock vs. healthy controls | All | 0.83 | 0.68 | $4.82 \times 10^{-20}$ | $0.90 \pm 0.08:0.97 \pm 0.05$ | 0.98:0.86 | 0.93 | 0.98 |
| | Infants | 0.92 | 0.78 | $2.15 \times 10^{-7}$ | $0.95 \pm 0.09:1.0$ | 1.0:0.92 | 0.97 | 1.0 |
| | Toddlers | 0.92 | 0.75 | $1.5 \times 10^{-7}$ | $0.90 \pm 0.14:1.0$ | 1.0:0.90 | 0.94 | 0.99 |
| | School age | 0.65 | 0.61 | $1.3 \times 10^{-4}$ | $0.92 \pm 0.14:0.89 \pm 0.2$ | 0.92:0.89 | 0.91 | 0.98 |
| Septic shock vs. SIRS/ICU controls | All | 0.46 | 0.28 | $4.5 \times 10^{-6}$ | $0.78 \pm 0.11:0.72 \pm 0.14$ | 0.80:0.68 | 0.75 | 0.82 |
| | Infants | 0.50 | 0.41 | $2.9 \times 10^{-4}$ | $0.91 \pm 0.13:0.62 \pm 0.26$ | 0.79:0.80 | 0.79 | 0.88 |
| | Toddlers | 0.53 | 0.30 | 0.026 | $0.63 \pm 0.22:0.69 \pm 0.23$ | 0.71:0.61 | 0.66 | 0.82 |
| | School age | 0.63 | 0.52 | 0.0013 | $0.92 \pm 0.14:0.88 \pm 0.23$ | 0.92:0.88 | 0.91 | 0.94 |

**R2Y metric describes the percentage of variation explained by the model; Q2 metric describes the predictive ability of the model. The difference between R2Y and Q2 indicates the model's goodness-of-fit. Sensitivity, specificity, PPV (positive predictive value), NPV (negative predictive value) and ACC (accuracy) were calculated based on the predictive values of Y-variables obtained in a sevenfold cross-validation step during OPLS-DA model construction. Sensitivity and specificity are reported with 95% confidence intervals. The AUROC (area under the ROC curve) statistic provides additional interpretation of discriminatory power of the models.

TABLE 3

List of potentially important metabolites based on the OPLS-DA regression coefficients ($p<0.05$) for models: SIRS/ICU controls vs. healthy, septic shock patients vs. healthy, septic shock patients vs. SIRS/ICU controls within infants, toddlers and school age children[+]

| | SIRS vs. Healthy | | | Septic vs. Healthy | | | Septic vs. SIRS | | |
|---|---|---|---|---|---|---|---|---|---|
| | Infants | Toddlers | School Age | Infants | Toddlers | School Age | Infants | Toddlers | School Age |
| 2-Aminobutyrate | ↓ | | ↓ | ↓ | ↓ | | | | |
| 2-Hydroxybutyrate | | | | ↑ | ↑ | ↑ | ↑ | | ↑ |
| 2-Hydroxyisobutyrate | ↑ | | | | | | | | |
| 2-Hydroxyisovalerate | ↑ | | | ↑ | ↑ | ↑ | | | |
| 2-Methylglutarate | | | | | ↑ | | | | |
| 2-Oxoisocaproate | ↑ | | | ↑ | | ↑ | | | ↑ |
| 3-Hydroxybutyrate | | ↑ | | | ↑ | | | | |
| 3-Hydroxyisovalerate | ↑ | | | | | | | | |
| Acetate | | ↓ | | ↓ | | | | | |
| Acetone | | ↑ | ↑ | | ↑ | | | | |
| Adipate | | | | ↓ | | | ↓ | | |
| Alanine | | | ↓ | | | | ↓ | | ↑ |
| Arginine | ↓ | | | | | ↑ | | ↑ | ↑ |
| Asparagine | | | | | | | | | ↑ |
| Betaine | | | | | ↑ | | | | |
| Carnitine | | | | | | ↑ | | | |
| Citrate | ↓ | ↓ | ↓ | | | ↓ | | ↑ | |
| Creatine | | | | | | ↑ | | | ↑ |
| Creatine phosphate | ↑ | | | | | ↑ | | | ↑ |
| Creatinine | ↑ | | | ↑ | | ↑ | | | ↑ |
| Ethanol | | | ↓ | | | | | | ↑ |
| Glucose | | | | ↑ | ↑ | | ↑ | ↑ | |
| Glutamate | | | | | | | ↓ | | |
| Glutamine | | ↓ | ↓ | | ↓ | | | | |
| Glycerol | ↓ | | | | | | ↑ | | ↑ |
| Glycine | ↑ | | | | | | ↓ | | |
| Histidine | | | | | | ↑ | | | ↑ |
| Hypoxanthine | | | | | | | ↓ | | |
| Isobutyrate | | ↑ | | | ↑ | | | | |
| Isoleucine | | | | | | | ↓ | | |
| Lactate | ↑ | ↑ | | ↑ | ↑ | ↑ | ↓ | | ↑ |
| Methanol | ↓ | ↓ | ↓ | | | | | | ↑ |

TABLE 3-continued

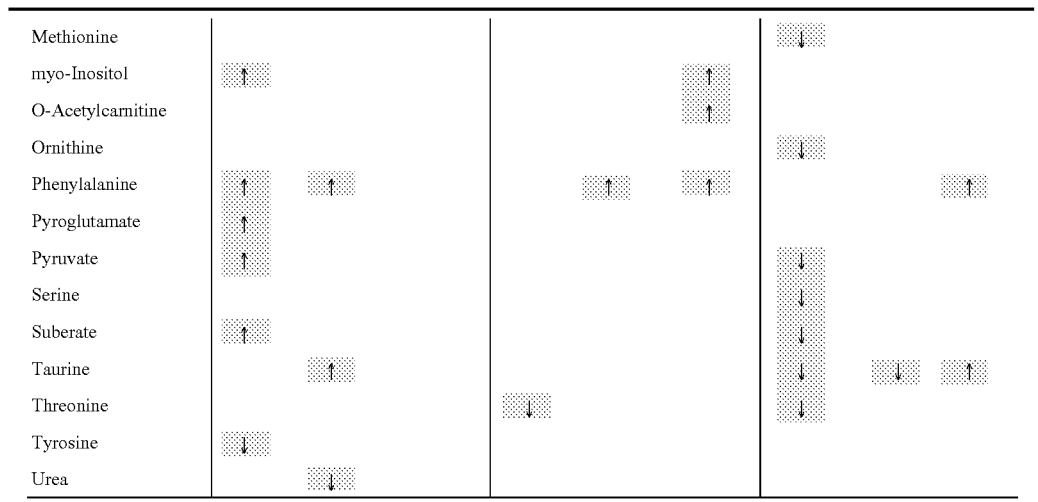

| Metabolite | | | | | | | |
|---|---|---|---|---|---|---|---|
| Methionine | | | | | | ↓ | |
| myo-Inositol | ↑ | | | | ↑ | | |
| O-Acetylcarnitine | | | | | ↑ | | |
| Ornithine | | | | | | ↓ | |
| Phenylalanine | ↑ | ↑ | | ↑ | ↑ | | ↑ |
| Pyroglutamate | ↑ | | | | | | |
| Pyruvate | ↑ | | | | | ↓ | |
| Serine | | | | | | ↓ | |
| Suberate | ↑ | | | | | ↓ | |
| Taurine | | ↑ | | | | ↓ | ↓ ↑ |
| Threonine | | | | ↓ | | ↓ | |
| Tyrosine | ↓ | | | | | | |
| Urea | | ↓ | | | | | |

†-Grey indicates significant change in the concentration (↑ - increased, ↓ - decreased), white - no significant change.

TABLE 4

Summary of the quality of the results for the mortality OPLS-DA models

| OPLS-DA mortality models | Quality results of the models | | | |
|---|---|---|---|---|
| | R2Y | Q2 | P value | AUROC |
| 20 septic shock specimens (10 non-survivors and 10 age-gender-matched survivors) | 0.63 | 0.47 | 0.0044 | 0.91 |
| 23 septic shock specimens with complicated course (10 non-survivors and 13 survivors) | 0.93 | 0.82 | 0.00043 | 1.0 |

TABLE 5

Comparison of sensitivity, specificity, PPV (positive predictive value), NPV (negative predictive value), ACC (accuracy) and AUROC results for models: septic shock patients vs. SIRS/ICU controls and nonsurvivors vs. survivors (age-gender-matched samples) based on metabolomics, PCT and PRISM III-APS data

| Model | Data | Sensitivity: Specificity | PPV:NPV | ACC | AUROC |
|---|---|---|---|---|---|
| Septic shock vs. SIRS/ICU controls | Metabolomics | 0.78 ± 0.11: 0.72 ± 0.14 | 0.80:0.68 | 0.75 | 0.82 |
| | PCT | 0.56 ± 0.16: 0.94 ± 0.08 | 0.91:0.66 | 0.74 | 0.80 |
| | PRISM III-APS | 0.83 ± 0.10: 0.56 ± 0.16 | 0.74:0.69 | 0.72 | 0.80 |
| Non-survivors vs. survivors (age-gender-matched samples) | Metabolomics | 0.80 ± 0.25: 0.90 ± 0.19 | 0.89:0.82 | 0.85 | 0.91 |
| | PCT | 0.29 ± 0.33: 0.57 ± 0.37 | 0.40:0.44 | 0.43 | 0.51 |
| | PRISM III-APS | 0.70 ± 0.28: 0.80 ± 0.25 | 0.78:0.73 | 0.75 | 0.85 |

Figure 8A:
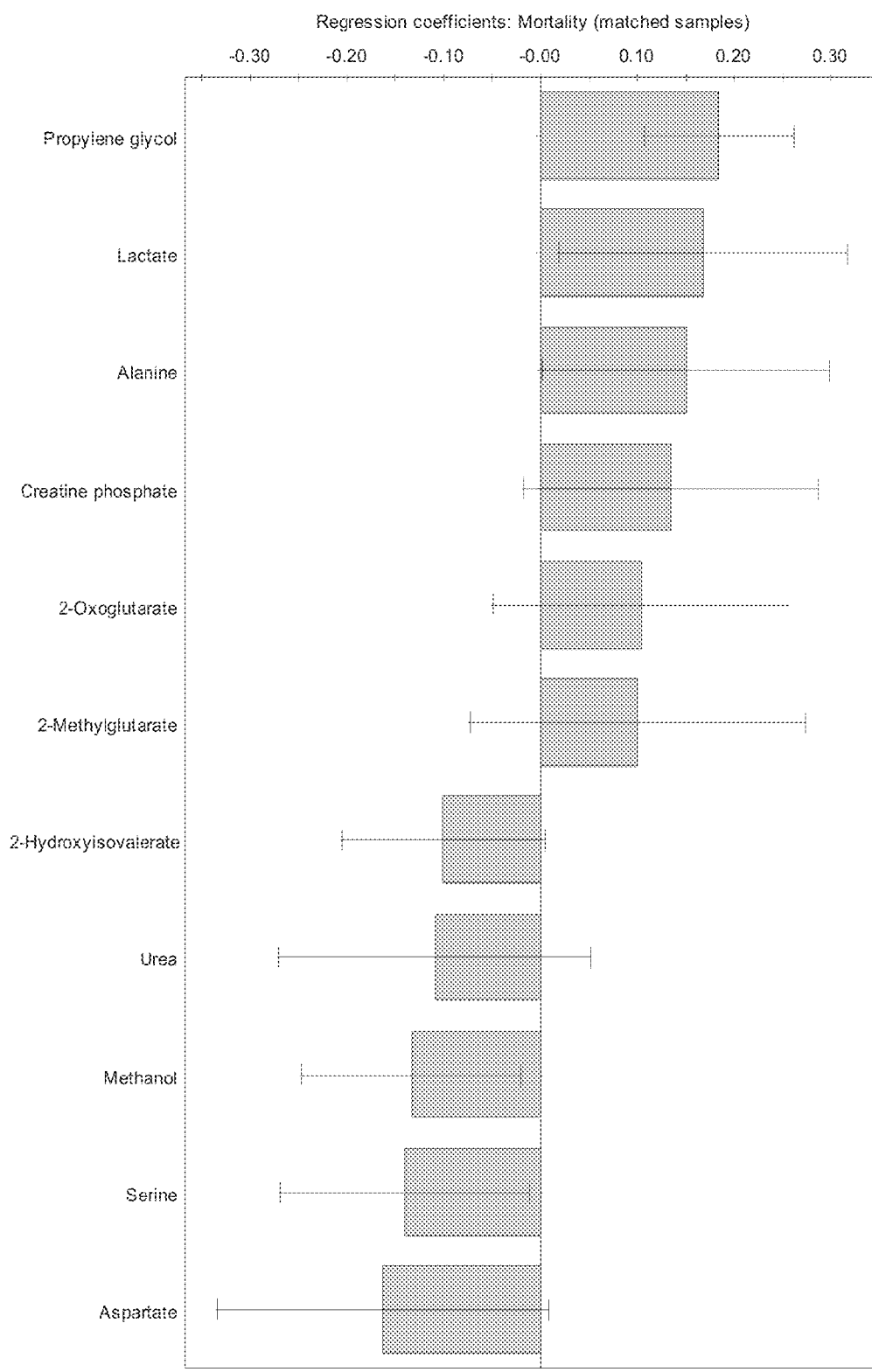
FIGS. 8A-B. OPLS regression coefficients plots.
Figure 8B:
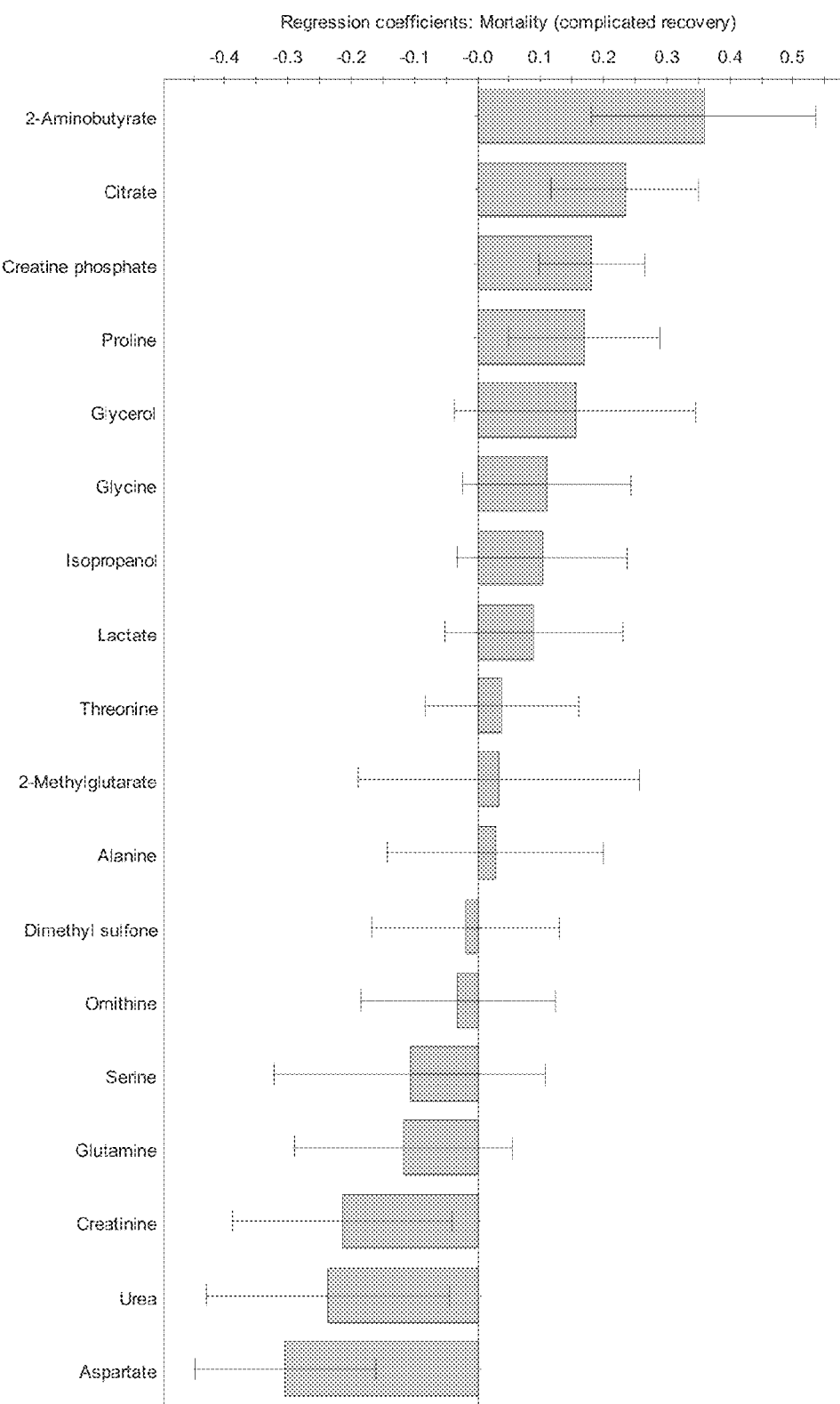

FIGS. 8A-B provide column plots showing the changes in serum metabolite concentrations in septic shock patients that predict mortality. FIG. 8A shows the data for age/gender-matched samples. FIG. 8B illustrates a complicated recovery course (i.e., ≥2 organ failures≥7 days after onset of septic shock). The data show increased metabolite concentrations in non-survivors (upper part of diagrams) and a decrease in metabolite concentrations in non-survivors, as compared survivors (lower part of diagrams).

Example 3

Discussion

This study describes a novel application of metabolomics for the diagnostic and prognostic evaluation of pediatric septic shock. The diagnosis of sepsis and septic shock remains a clinical challenge in pediatric critical care, especially because of the disease's complexity and heterogeneity in this population. Additionally, there is no other factor more crucial in the recognition of septic shock than time. However, making a firm diagnosis early is critical since early recognition of septic shock and rapid medical intervention may significantly improve patients' outcomes and increase their chance for survival [9, 30]. Consequently, a global health initiative has been created that aims to develop a multifaceted medical approach and aims to identify effective biomarkers in order to aid in the early diagnosis and treatment of septic shock and to improve the quality of clinical care for children with sepsis syndrome [7, 31]. It seems clear that early identification of factors that influence the outcome in pediatric septic shock may improve early diagnosis and treatment of children who are at the highest risk of death. Therefore, research and actions that open the door to quick recognition of pediatric septic shock in PICU is an important goal, and a goal of this study.

In this work, the inventors were able to separate septic shock patients from non-infected PICU patients (with SIRS) and healthy children using serum samples and an NMR-based metabolomics approach. Both septic shock serum samples and SIRS/ICU control serum samples were collected within 24 hours of admission to PICU allowing for early diagnostic and prognostic evaluation of the disease. Metabolomics has been previously suggested as a potential technique for early diagnosis of sepsis [17-19], but this appears to be the first study that uses serum metabolomics to evaluate septic shock in a pediatric population. It is certainly the largest pediatrics metabolomics study. In addition there is currently no other study in the literature that describes analysis of metabolic profiles within the three patient groups: septic shock, SIRS/ICU controls and healthy pediatric controls. The inventors present models that consist of only two groups of patients: SIRS/ICU patients and healthy controls, septic shock patients and healthy controls or septic shock patients and SIRS/ICU controls, and these groupings resulted in differences in serum metabolite concentrations depending on the age of the studied subjects. Infants and toddlers demonstrated quite similar metabolic response to septic shock whereas OPLS-DA models consisting of school age children showed different results than those obtained from younger patient groups. Interestingly, it has recently been published in an age-specific transcriptomics study of children with septic shock, that the school age children had a much larger number of uniquely regulated gene sets relative to age-matched controls than infants and toddlers [32]. Therefore, it should not be a surprise that using a metabolomic profiling approach followed a very similar pattern as that revealed by a whole blood transcriptomic response approach during pediatric septic shock.

Some metabolite concentrations changed markedly in specific groups significantly influencing the separation between healthy and septic shock patients. Three compounds: 2-hydroxybutyrate, 2-hydroxyisovalerate and lactate show elevated levels in the model consisting of septic shock patient vs. healthy controls regardless of differences in the age (Table 3). These metabolites are mainly associated with increasing demands for energy during infections and inflammatory conditions and their high concentrations indicate enhanced fat breakdown resulting in a tendency towards ketoacidosis and lactic acidosis in septic shock critically ill patients [33-35]. However, more characteristic biopatterns might be described within specific age categories. In the infant and toddler groups significantly higher levels of glucose were detected in septic shock patients compare to both of the control groups: healthy and SIRS/ICU controls (Table 3). It is well known that uncontrolled and expanding inflammatory responses in sepsis causes hyperglycemia, thus detection of elevated serum glucose was expected. Additionally, for school age children there were many other metabolites which concentration increased markedly in septic shock patients vs. healthy or SIRS/ICU controls (Table 3). The elevated levels of 2-oxoisocaproate, creatine, creatine phosphate, creatinine, histidine and phenylalanine are mainly associated with an enhanced muscular protein turnover, amino acids oxidation, decreased energy supply and organ failure during septic shock [36-40]. An increased concentration of arginine in the septic shock patients might be related to cytokine production. It is known that the inflammatory process is modulated by nitric oxide (NO) which is formed from arginine [41] and extracellular arginine availability is crucial for NO synthesis [42] thus there is a very close relationship between arginine concentration and NO formation [43]. Taken together, the metabolites described above may be considered as biomarkers for an early diagnosis of septic shock in PICU patients.

The inventors also evaluated whether a NMR-based metabolomics approach could be applied to define metabolic variation between septic shock survivors and non-survivors. According to the International Pediatric Sepsis Consensus Conference panel discussion [29], mortality is the most important clinical outcome in sepsis. Clearly, mortality should not be the only considered end point and thus should be studied with other factors or scores examining patient survival. There are several scoring systems for estimating pediatric organ dysfunction and children's mortality, for example the Pediatric Logistic Organ Dysfunction (PELOD) score [44, 45], the Multiple Organ System Failure (MOSF) score [46] or the Pediatric Risk of Mortality (PRISM) score [47]. The PRISM score, a physiology-based measurement, is the most common currently available system used for mortality prediction in PICU. Recently, the PRISM score was upgraded to PRISM III-APS (PRISM III-Acute Physiology Score) including new treatment protocols, therapeutic interventions and is a measure of physiologic instability that has been validated against mortality [48, 49]. Despite all efforts to improve a sepsis mortality scoring system, determining reliable mortality risk is still challenging and a very difficult process early in the clinical setting. In our study the constructed metabolomics models show an excellent separation between survivors and non-survivors and a very good distinction between observed and expected outcomes.

It should be noted that this study is just an initial step in pediatric mortality risk assessment using a metabolomics approach as it refers to data collected from only a small number of patients. Although one can criticize this study as being a small study, it is the largest pediatric metabolomics study we have found to date. Pediatric studies of 140 patients are generally thought of as reasonably sized studies as pediatric studies generally do not include as many patients as adult studies do. None-the-less, the profiling method applied in this study should be validated by a larger cohort of PICU patients in future research. It should be further noted that other methods of metabolomics analysis can be used, such as gas chromatography mass-spectroscopy or liquid chromatography mass-spectroscopy, which may yield other or more features or metabolites that could enhance the separation between the groups presented in this NMR-based study.

In conclusion, this study presents metabolomics as a promising method for diagnostic and early prognostic evaluation of septic shock patients in PICU. These findings show that septic shock leads to significant disruption in biochemical homeostasis that strongly contributes to changes in body metabolites. Moreover, these data strongly suggested that metabolic profiling be used as an additional methodology for the early diagnosis and prognosis of septic shock in PICU. However, it is suggested that this application should be further evaluated using a larger cohort of critical ill patients. Nonetheless, metabolomics should be considered as a very capable application in the development of better strategies of septic shock diagnosis and prognosis in PICU. Because of the non-invasive nature of the analysis, it is recommended that metabolic profiling be further studied as a technique for early diagnosis of septic shock and prediction of outcome in PICU.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention as defined by the appended claims.

V. References

The following references, to the extent that they provide exemplary procedural or other details supplementary to those set forth herein, are specifically incorporated herein by reference:

1. Pollack M M, Fields A I, Ruttimann U E. Sequential cardiopulmonary variables of infants and children in septic shock, *Crit Care Med* 1984; 12(7): 554-9.

2. Pollack M M, Fields A I, Ruttimann U E. Distributions of cardiopulmonary variables in pediatric survivors and non-survivors of septic shock. *Crit Care Med* 1985; 13(6): 454-9.
3. Czaja A S, Zimmerman J J, Nathens A B. Readmission and late mortality after pediatric severe sepsis. *Pediatrics* 2009; 123(3): 849-57.
4. Watson R S, Carcillo J A, Linde-Zwirble W T, Clermont G, Lidicker J, Angus D C. The epidemiology of severe sepsis in children in the United States. *Am J Respir Crit Care Med* 2003; 167(5): 695-701.
5. Lodha R, Oleti T P, Kabra S K. Management of septic shock. *Indian J Pediatr* 2011; 78(6): 726-33.
6. Singh D, Chopra A, Pooni P A, Bhatia R C. A clinical profile of shock in children in Punjab, India. *Indian Pediatr* 2006; 43(7): 619-23.
7. Smits A, Jin Z, Elsir T, Pedder H, Nister M, Alafuzoff I, Dimberg A, Edqvist P H, Ponten F, Aronica E, Birnir B. GABA-A channel subunit expression in human glioma correlates with tumor histology and clinical outcome. *PLoS One* 2012; 7(5): e37041.
8. Lawrence K. Pediatric sepsis and multiorgan dysfunction syndrome: progress and continued challenges. *Crit Care Nurs Clin North Am* 2011; 23(2): 323-37.
9. Rivers E, Nguyen B, Haystad S, Ressler J, Muzzin A, Knoblich B, Peterson E, Tomlanovich M. Early goal-directed therapy in the treatment of severe sepsis and septic shock *N Engl J Med* 2001; 345(19): 1368-77.
10. Brierley J, Carcillo J A, Choong K, Cornell T, Decaen A, Deymann A, Doctor A, Davis A, Duff J, Dugas M A, Duncan A, Evans B, Feldman J, Felmet K, Fisher G, Frankel L, Jeffries H, Greenwald B, Gutierrez J, Hall M, Han Y Y, Hanson J, Hazelzet J, Hernan L, Kiff J, Kissoon N, Kon A, Irazurta J, Lin J, Lorts A, Mariscalco M, Mehta R, Nadel S, Nguyen T, Nicholson C, Peters M, Okhuysen-Cawley R, Poulton T, Relves M, Rodriguez A, Rozenfeld R, Schnitzler E, Shanley T, Kache S, Skippen P, Tones A, von Dessauer B, Weingarten J, Yeh T, Zaritsky A, Stojadinovic B, Zimmerman J, Zuckerberg A. Clinical practice parameters for hemodynamic support of pediatric and neonatal septic shock: 2007 update from the American College of Critical Care Medicine. *Crit Care Med* 2009; 37(2): 666-88.
11. Han Y Y, Carcillo J A, Dragotta M A, Bills D M, Watson R S, Westerman M E, Orr R A. Early reversal of pediatric-neonatal septic shock by community physicians is associated with improved outcome. *Pediatrics* 2003; 112(4): 793-9.
12. Trzeciak S, McCoy J V, Phillip Dellinger R, Arnold R C, Rizzuto M, Abate N L, Shapiro N I, Parrillo J E, Hollenberg S M. Early increases in microcirculatory perfusion during protocol-directed resuscitation are associated with reduced multi-organ failure at 24 h in patients with sepsis. *Intensive Care Med* 2008; 34(12): 2210-7.
13. Lindon J C, Holmes E, Bollard M E, Stanley E G, Nicholson J K. Metabonomics technologies and their applications in physiological monitoring, drug safety assessment and disease diagnosis. *Biomarkers* 2004; 9(1): 1-31.
14. Nicholson J K, Lindon J C, Holmes E. 'Metabonomics': understanding the metabolic responses of living systems to pathophysiological stimuli via multivariate statistical analysis of biological NMR spectroscopic data. *Xenobiotica* 1999; 29(11): 1181-9.
15. Laiakis E C, Morris G A, Formace A J, Howie S R. Metabolomic analysis in severe childhood pneumonia in the Gambia, West Africa: findings from a pilot study. *PLoS One* 2010; 5(9).
16. Godoy M M, Lopes E P, Silva R O, Hallwass F, Koury L C, Moura I M, Goncalves S M, Simas A M. Hepatitis C virus infection diagnosis using metabonomics. *J Viral Hepat* 2010; 17(12): 854-8.
17. Izquierdo-Garcia J L, Nin N, Ruiz-Cabello J, Rojas Y, de Paula M, Lopez-Cuenca S, Morales L, Martinez-Caro L, Fernandez-Segoviano P, Esteban A, Lorente J A. A metabolomic approach for diagnosis of experimental sepsis. *Intensive Care Med* 2011.
18. Lin Z Y, Xu P B, Yan S K, Meng H B, Yang G J, Dai W X, Liu X R, Li J B, Deng X M, Zhang W D. A metabonomic approach to early prognostic evaluation of experimental sepsis by (1) H NMR and pattern recognition. *NMR Biomed* 2009; 22(6): 601-8.
19. Xu P B, Lin Z Y, Meng H B, Yan S K, Yang Y, Liu X R, Li J B, Deng X M, Zhang W D. A metabonomic approach to early prognostic evaluation of experimental sepsis. *J Infect* 2008; 56(6): 474-81.
20. Weljie A M, Newton J, Mercier P, Carlson E, Slupsky C M. Targeted profiling: quantitative analysis of 1H NMR metabolomics data. *Anal Chem* 2006; 78(13): 4430-42.
21. Eriksson L, Johansson E, Kettaneh-Wold N, Trygg J, Wikström C, Wold S, *Multi-and Megavariate Data Analysis Part I: Basic Principles and Applications*. 2006, Umeå, Sweden: Umetrics A B. 425.
22. Trygg J, Wold S. Orthogonal projections to latent structures (O-PLS). *J Chemometrics* 2002; 16(3): 119-28.
23. Kramer R, *Chemometric techniques for quantitative analysis*. 1998, New York, USA: Marcel Dekker, Inc.
24. Mickiewicz B, Wong H R, Vogel H J, Winston B W. Metabolomic profiling of serum samples by $^1$H NMR spectroscopy as a novel approach for diagnosis of pediatric septic shock. *Am. J. Respir. Crit. Care Med.* 2012; 185: A4911.
25. Nicholson J K, Foxall P J, Spraul M, Farrant R D, Lindon J C. 750 MHz 1H and 1H-13C NMR spectroscopy of human blood plasma. *Anal Chem* 1995; 67(5): 793-811.
26. Dieterle F, Ross A, Schlotterbeck G, Senn H. Probabilistic quotient normalization as robust method to account for dilution of complex biological mixtures. Application in 1H NMR metabonomics. *Anal Chem* 2006; 78(13): 4281-90.
27. Picard R R, Cook D R. Cross-Validation of Regression Models. *Journal of the American Statistical Association* 1984; 79(387): 575-83.
28. Fawcett T. An introduction to ROC analysis. *Pattern Recognition Letters* 2006; 27(8): 861-874.
29. Goldstein B, Giroir B, Randolph A. International pediatric sepsis consensus conference: definitions for sepsis and organ dysfunction in pediatrics. *Pediatr Crit Care Med* 2005; 6(1): 2-8.
30. Carcillo J A, Davis A L, Zaritsky A. Role of early fluid resuscitation in pediatric septic shock. *Jama* 1991; 266(9): 1242-5.
31. Kissoon N, Carcillo J A, Espinosa V, Argent A, Devictor D, Madden M, Singhi S, van der Voort E, Latour J. World Federation of Pediatric Intensive Care and Critical Care Societies: Global Sepsis Initiative. *Pediatr Crit Care Med* 2011; 12(5): 494-503.
32. Wynn J L, Cvijanovich N Z, Allen G L, Thomas N J, Freishtat R J, Anas N, Meyer K, Checchia P A, Lin R, Shanley T P, Bigham M T, Banschbach S, Beckman E, Wong H R. The influence of developmental age on the early transcriptomic response of children with septic shock. *Mol Med* 2011; 17(11-12): 1146-56.
33. Liebich H M, Forst C. Hydroxycarboxylic and oxocarboxylic acids in urine: products from branched-chain amino acid degradation and from ketogenesis. *J Chromatogr* 1984; 309(2): 225-42.
34. Landaas S, Pettersen J E. Clinical conditions associated with urinary excretion of 2-hydroxybutyric acid. *Scand J Clin Lab Invest* 1975; 35(3): 259-66.
35. Mizock B A, Falk J L. Lactic acidosis in critical illness. *Crit Care Med* 1992; 20(1): 80-93.
36. Kovarik M, Muthny T, Sispera L, Holecek M. Effects of beta-hydroxy-beta-methylbutyrate treatment in different types of skeletal muscle of intact and septic rats. *J Physiol Biochem* 2010; 66(4): 311-9.
37. Wishart D S, Knox C, Guo A C, Eisner R, Young N, Gautam B, Hau D D, Psychogios N, Dong E, Bouatra S, Mandal R, Sinelnikov I, Xia J, Jia L, Cruz J A, Lim E, Sobsey C A, Shrivastava S, Huang P, Liu P, Fang L, Peng J, Fradette R, Cheng D, Tzur D, Clements M, Lewis A, De Souza A, Zuniga A, Dawe M, Xiong Y, Clive D, Greiner R, Nazyrova A, Shaykhutdinov R, Li L, Vogel H J, Forsythe I. HMDB: a knowledgebase for the human metabolome. *Nucleic Acids Res* 2009; 37 (Database issue): D603-10.
38. Hasselgren P O, Talamini M, James J H, Fischer J E. Protein metabolism in different types of skeletal muscle during early and late sepsis in rats. *Arch Surg* 1986; 121(8): 918-23.
39. Wannemacher R W, Jr., Klainer A S, Dinterman R E, Beisel W R. The significance and mechanism of an increased serum phenylalanine-tyrosine ratio during infection. *Am J Clin Nutr* 1976; 29(9): 997-1006.
40. Goldman R. The clinical evaluation of renal function. *Calif Med* 1956; 85(6): 376-80.
41. Knowles R G, Moncada S, Nitric oxide synthases in mammals. *Biochem J* 1994; 298 (Pt 2): 249-58.
42. Bruins M J, Lamers W H, Meijer A J, Soeters P B, Deutz N E. In vivo measurement of nitric oxide production in porcine gut, liver and muscle during hyperdynamic endotoxaemia. *Br J Pharmacol* 2002; 137(8): 1225-36.
43. Wu G, Flynn N E, Flynn S P, Jolly C A, Davis P K. Dietary protein or arginine deficiency impairs constitutive and inducible nitric oxide synthesis by young rats. *J Nutr* 1999; 129(7): 1347-54.
44. Leteurtre S, Martinot A, Duhamel A, Proulx F, Grandbastien B, Cotting J, Gottesman R, Joffe A, Pfenninger J, Hubert P, Lacroix J, Leclerc F. Validation of the paediatric logistic organ dysfunction (PELOD) score: prospective, observational, multicenter study. *Lancet* 2003; 362(9379): 192-7.
45. Leteurtre S, Duhamel A, Grandbastien B, Lacroix J, Leclerc F. Paediatric logistic organ dysfunction (PELOD) score. *Lancet* 2006; 367(9514): 897; author reply 900-2.
46. Wilkinson J D, Pollack M M, Glass N L, Kanter R K, Katz R W, Steinhart C M. Mortality associated with multiple organ system failure and sepsis in pediatric intensive care unit. *J Pediatr* 1987; 111(3): 324-8.
47. Pollack M M, Ruttimann U E, Getson P R. Pediatric risk of mortality (PRISM) score. *Crit Care Med* 1988; 16(11): 1110-6.
48. Pollack M M, Patel K M, Ruttimann U E. The Pediatric Risk of Mortality III—Acute Physiology Score (PRISM III-APS): a method of assessing physiologic instability for pediatric intensive care unit patients. *J Pediatr* 1997; 131 (4): 575-81.
49. Pollack M M, Patel K M, Ruttimann U E. PRISM III: an updated Pediatric Risk of Mortality score. *Crit Care Med* 1996; 24(5): 743-52.
50. Wong, H. R., et al., Genome-level expression profiles in pediatric septic shock indicate a role for altered zinc homeostasis in poor outcome. *Physiol Genomics,* 2007. 30(2): p. 146-55.
51. Goldstein B, Giroir B, Randolph A. International pediatric sepsis consensus conference: definitions for sepsis and organ dysfunction in pediatrics. *Pediatr Crit Care Med* 2005; 6(1): 2-8.
52. Pollack M M, Patel K M, Ruttimann U E. The Pediatric Risk of Mortality III-Acute Physiology Score (PRISM III-APS): a method of assessing physiologic instability for pediatric intensive care unit patients. *J Pediatr* 1997; 131 (4): 575-81.
53. Xiao W, Mindrinos M N, Seok J, Cuschieri J, Cuenca A G, Gao H, Hayden D L, Hennessy L, Moore E E, Minei J P, Bankey P E, Johnson J L, Sperry J, Nathens A B, Billiar T R, West M A, Brownstein B H, Mason P H, Baker H V, Finnerty C C, Jeschke M G, López M C, Klein M B, Gamelli R L, Gibran N S, Arnoldo B, Xu W, Zhang Y, Calvano S E, McDonald-Smith G P, Schoenfeld D A, Storey J D, Cobb J P, Warren H S, Moldawer L L, Herndon D N, Lowry S F, Maier R V, Davis R W, Tompkins R G; Inflammation and Host Response to Injury Large-Scale Collaborative Research Program. A genomic storm in critically injured humans. *J Exp Med,* 2011; 208(13): 2581-90.

The invention claimed is:
1. A method of differentiating a pediatric subject with pediatric septic shock from a healthy pediatric subject comprising:
 (a) obtaining a serum sample from said subject;
 (b) subjecting said sample to nuclear magnetic resonance (NMR) analysis of 2-hydroxybutyrate, 2-hydroxyisovalerate and lactate levels; and
 (c) diagnosing said subject as having pediatric shock when 2-hydroxybutyrate, 2-hydroxyisovalerate and lactate levels in said subject are elevated as compared to levels in a healthy pediatric subject.
2. The method of claim 1, wherein said subject is an infant or toddler.
3. The method of claim 1, wherein said subject is an infant, toddler or school age.
4. The method of claim 1, wherein said subject is an infant or school age.
5. The method of claim 1, wherein said subject is an infant.
6. The method of claim 1, wherein said subject is a toddler.
7. The method of claim 1, wherein said subject is a toddler or school age.
8. The method of claim 1, further comprising NMR analysis of 2-aminobutyrate, 2-oxoisocaproate, glucose, creatinine and/or phenylalanine.
9. The method of claim 1, further comprising NMR analysis of 2-methylglutarate, acetone, adipate, arginine, betaine, carnitine, citrate, creatine, creatine phosphate, glutamine, histidine, hypoxanthine, isobutyrate, myo-inositol, o-acetylcarnitine and/or threonine.
10. The method of claim 1, further comprising treating said subject for pediatric septic shock when diagnosed as having pediatric septic shock.
11. A method of differentiating a pediatric subject with sudden inflammatory response syndrome (SIRS) from a healthy subject having comprising:
 (a) obtaining a serum from said subject;
 (b) subjecting said sample to nuclear magnetic resonance (NMR) analysis of methanol and citrate; and
 (c) diagnosing said subject as having SIRS when levels of methanol and citrate are reduced as compared to levels in a healthy pediatric subject.

12. The method of claim 1, wherein said subject is an infant, toddler or school age.

13. The method of claim 1, further comprising NMR analysis of 2-aminobutyrate, acetone, glutamine, lactate, and/or phenylalanine.

14. The method of claim 1, further comprising NMR analysis of 2-hydroxyisobutyrate, 2-hydroxyisovalerate, 2-oxoisocaproate, 2-hydroxybutyrate, 3-hydroxyisovalerate, acetate, alanine, arginine, creatine phosphate, creatinine, ethanol, glycerol, glycerin, isobutyrate, myo-inositol, pyroglutamate, pyruvate, suberate, taurine, tyrosine and/or urea.

15. The method of claim 1, further comprising treating said subject for SIRS when diagnosed as having SIRS.

16. A method of predicting mortality in a pediatric sepsis patient comprising:
(a) obtaining a serum sample from said subject;
(b) subjecting said sample to nuclear magnetic resonance (NMR) analysis of lactate, alanine, creatine phosphate, 2-methyglutarate, urea, serine and aspartate levels; and
(c) predicting mortality when lactate, alanine, creatine phosphate and 2-methyglutarate levels in said subject are elevated, and urea serine and aspartate levels are reduced in said subject, both as compared to levels observed in pediatric septic shock survivors.

17. The method of claim 16, wherein said subject is an infant, toddler or school age.

18. The method of claim 16, further comprising NMR analysis of 2-aminobutyrate, acetone, glutamine, lactate, and/or phenylalanine.

19. The method of claim 16, further comprising NMR analysis of 2-aminobutyrate, citrate, praline, glycerol, glycine, isopropanol, threonine, dimethyl sulfone, ornithine, glutamine and/or creatine.

20. The method of claim 16, further comprising treating said subject for pediatric septic shock.

* * * * *

UNITED STATES PATENT AND TRADEMARK OFFICE
CERTIFICATE OF CORRECTION

PATENT NO.        : 8,969,017 B2                                Page 1 of 1
APPLICATION NO.   : 14/160712
DATED             : March 3, 2015
INVENTOR(S)       : Beata Mickiewicz et al.

It is certified that error appears in the above-identified patent and that said Letters Patent is hereby corrected as shown below:

In the Claims

In claim 1, column 28, line 34, delete "pediatric shock" and insert --pediatric septic shock-- therefor.

In claim 11, column 28, line 61, delete "having".

In claim 11, column 28, line 62, delete "serum" and insert --serum sample-- therefor.

In claim 16, column 30, line 3, delete "urea serine" and insert --urea, serine-- therefor.

In claim 19, column 30, line 12, delete "praline" and insert --proline-- therefor.

Signed and Sealed this
Sixteenth Day of June, 2015

Michelle K. Lee
*Director of the United States Patent and Trademark Office*